(12) United States Patent
Lim et al.

(10) Patent No.: US 11,511,997 B2
(45) Date of Patent: Nov. 29, 2022

(54) ELECTROPHORETIC DISPLAY

(71) Applicant: Lyten, Inc., Sunnyvale, CA (US)

(72) Inventors: Sung H. Lim, Mountain View, CA (US); Michael W. Stowell, Sunnyvale, CA (US); Bruce Lanning, Littleton, CO (US)

(73) Assignee: Lyten, Inc., San Jose, CA (US)

( * ) Notice: Subject to any disclaimer, the term of this patent is extended or adjusted under 35 U.S.C. 154(b) by 407 days.

(21) Appl. No.: 16/888,506

(22) Filed: May 29, 2020

(65) Prior Publication Data

US 2020/0292488 A1    Sep. 17, 2020

Related U.S. Application Data

(63) Continuation-in-part of application No. 16/706,542, filed on Dec. 6, 2019, now Pat. No. 10,955,378, and
(Continued)

(51) Int. Cl.
*C01B 32/18* (2017.01)
*C01B 32/182* (2017.01)
(Continued)

(52) U.S. Cl.
CPC ......... *C01B 32/18* (2017.08); *B01J 20/28066* (2013.01); *C01B 32/182* (2017.08);
(Continued)

(58) Field of Classification Search
CPC ..... C01B 32/18; C01B 32/182; C01B 32/194; C01B 2204/22; C01B 2204/04;
(Continued)

(56) References Cited

U.S. PATENT DOCUMENTS 5,150,080 A    9/1992   Bianchini et al.
6,359,444 B1   3/2002   Grimes
(Continued)

FOREIGN PATENT DOCUMENTS

KR    10-2012-0002925 A    1/2012
KR    10-2017-0112545 A    10/2017
KR       10-1913709 B1    11/2018

OTHER PUBLICATIONS

Lee, S. et al., "Three-Dimensional Self-Assembly of Graphene Oxide Platelets into Mechanically Flexible Macroporous Carbon Films", Angew. Chem. Int. Ed., vol. 49; 2010; DOI: 10.1002/anie.201006240; 6 pages.
(Continued)

*Primary Examiner* — Jimmy H Nguyen
(74) *Attorney, Agent, or Firm* — Paradice & Li LLP

(57) ABSTRACT

This disclosure provides an electrophoretic display system including a first electrode disposed on a substrate and a three-dimensional (3D) carbon-based structure configured to guide a migration of electrically charged electrophoretic ink particles dispersed therein that are configured to be responsive to application of a voltage to the first electrode. The 3D carbon-based structure includes a plurality of 3D aggregates defined by a morphology of graphene nanoplatelets orthogonally fused together and cross-linked by a polymer; and, a plurality of channels interspersed throughout the 3D carbon-based structure defined by the morphology. The plurality of channels includes a plurality of inter-particle pathways and a plurality of intra-particle pathways. Each inter-particle pathway can include a smaller dimension than each inter-particle pathway. A second electrode is disposed on the 3D carbon-based structure. Each 3D aggregate can include any one or more of graphene, carbon nano-onions, carbon nano-platelets, or carbon nanotubes.

19 Claims, 23 Drawing Sheets

Related U.S. Application Data a continuation-in-part of application No. 16/282,895, filed on Feb. 22, 2019, now Pat. No. 10,763,586, said application No. 16/706,542 is a continuation of application No. 16/239,423, filed on Jan. 3, 2019, now Pat. No. 10,502,705, said application No. 16/282,895 is a continuation of application No. 15/944,482, filed on Apr. 3, 2018, now Pat. No. 10,218,073.

(60) Provisional application No. 62/866,464, filed on Jun. 25, 2019, provisional application No. 62/815,927, filed on Mar. 8, 2019, provisional application No. 62/613,716, filed on Jan. 4, 2018, provisional application No. 62/508,295, filed on May 18, 2017, provisional application No. 62/482,806, filed on Apr. 7, 2017, provisional application No. 62/481,821, filed on Apr. 5, 2017.

(51) Int. Cl.

| | | |
|---|---|---|
| *B01J 20/28* | (2006.01) | |
| *G02F 1/167* | (2019.01) | |
| *C09D 5/44* | (2006.01) | |
| *C25D 13/02* | (2006.01) | |
| *G09G 3/34* | (2006.01) | |
| *C01B 32/194* | (2017.01) | |
| *G02F 1/1675* | (2019.01) | |
| *G02F 1/165* | (2019.01) | |
| *G01N 33/00* | (2006.01) | |

(52) U.S. Cl.
CPC .............. *C01B 32/194* (2017.08); *C09D 5/44* (2013.01); *C25D 13/02* (2013.01); *G02F 1/165* (2019.01); *G02F 1/167* (2013.01); *G02F 1/1675* (2019.01); *G09G 3/344* (2013.01); *C01B 2204/04* (2013.01); *C01B 2204/22* (2013.01); *C01B 2204/32* (2013.01); *G01N 33/004* (2013.01); *G01N 33/0037* (2013.01); *G01N 33/0039* (2013.01); *G01N 33/0044* (2013.01); *G02F 2001/1678* (2013.01)

(58) Field of Classification Search
CPC ... C01B 2204/32; G02F 1/165; G02F 1/1675; G02F 1/167; G02F 2001/1678; B01J 20/28066; G09G 3/344; C25D 13/02; C09D 5/44; G01N 33/0044; G01N 33/004; G01N 33/0037; G01N 33/0039
USPC .......................................... 359/296; 345/107
See application file for complete search history.

(56) References Cited

U.S. PATENT DOCUMENTS

| | | | |
|---|---|---|---|
| 8,281,642 | B2 | 10/2012 | Lee et al. |
| 9,208,928 | B2 | 12/2015 | Muramatsu |
| 9,502,711 | B2 | 11/2016 | Fang et al. |
| 9,576,694 | B2 | 2/2017 | Gogotsi et al. |
| 10,034,382 | B2 | 7/2018 | Yan et al. |
| 2004/0113846 | A1 | 6/2004 | Achim |
| 2007/0068493 | A1 | 3/2007 | Pavlovsky |
| 2009/0145233 | A1 | 6/2009 | Eklund et al. |
| 2011/0310465 | A1 | 12/2011 | Takanashi et al. |
| 2015/0279504 | A1 | 10/2015 | Viville et al. |
| 2019/0143105 | A1* | 5/2019 | Liu ..................... A61N 1/0428 204/601 |

OTHER PUBLICATIONS

Zhang, Y. et al., "Fast-response and monodisperse silica nanoparticles modified with ionic liquid towards electrophoretic displays", Dyes and Pigments, vol. 148, Jan. 2018; pp. 270-275.

* cited by examiner

*Not Drawn to Scale

Key Features 1500B

- Top electrode (850) formed by optically-transparent conductors (conductive but no Ag)
- Patterned micro-cups/microcapsules/recessed regions (935)
- Solvent-resistant layers (first electrode layer 820, second electrode layer 850)
- All transparent components made with carbon-containing materials (such as the carbon matrix 830)

*FIG. 15B*

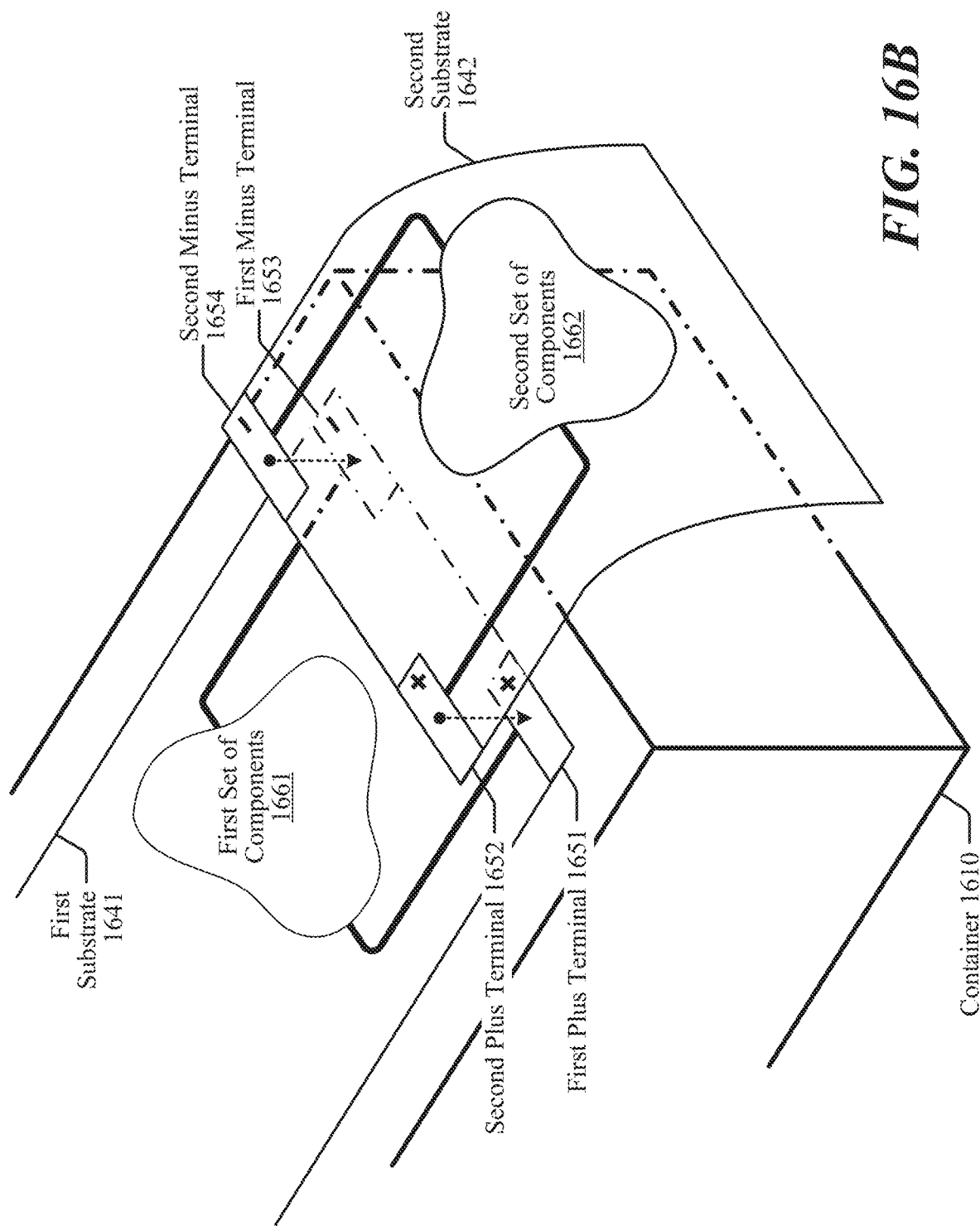

ELECTROPHORETIC DISPLAY

RELATED APPLICATIONS

This application claims priority to U.S. Provisional Patent Application No. 62/866,464 entitled "Electrophoretic Display" filed on Jun. 25, 2019 and this application is a continuation-in-part to U.S. patent application Ser. No. 16/706,542 filed on Dec. 6, 2019 entitled "Resonant Gas Sensor", which claims priority to U.S. Provisional Patent Application No. 62/815,927, filed on Mar. 8, 2019 entitled "Resonant Gas Sensor", and which is a continuation of U.S. patent application Ser. No. 16/239,423 filed Jan. 3, 2019 entitled "Resonant Gas Sensor", which claims priority to U.S. Provisional Patent Application No. 62/613,716, filed Jan. 4, 2018 entitled "Volatiles Sensor"; and this application is a continuation-in-part of and claims the benefit of priority to U.S. patent application Ser. No. 16/282,895, filed Feb. 22, 2019, entitled "Antenna with Frequency-Selective Elements", which is a continuation of U.S. patent application Ser. No. 15/944,482 filed Apr. 3, 2018, entitled "Antenna with Frequency-Selective Elements", which claims priority to U.S. Provisional Patent Application No. 62/508,295 filed May 18, 2017 entitled "Carbon-Based Antenna", and which claims priority to U.S. Provisional Patent Application No. 62/482,806 filed Apr. 7, 2017 entitled "Dynamic Energy Harvesting Power Architecture", and which claims priority to U.S. Provisional Patent Application No. 62/481,821 filed Apr. 5, 2017 entitled "Dynamic Energy Harvesting Power Architecture"; all of which are hereby incorporated by reference their respective entireties for all purposes.

TECHNICAL FIELD

This disclosure relates generally to an electrophoretic display, and more specifically, to an electrophoretic display device that includes carbon particles that are cross-linked with each other by a polymer and, upon activation, mimics the appearance of traditional ink on paper.

DESCRIPTION OF RELATED ART

Electrophoretic displays (EPDs), also referred to as electronic paper, offer a low-energy consumption alternative to traditional flat-panel displays and have therefore become widely used in various consumer products including electronic reading devices, digital notepads, shelf labels, signs and simple displays suitable for use on packaging or as digital labels. Unlike conventional backlit flat panel displays that emit light, EPDs reflect light like traditional paper. This may make them more comfortable to read and provides a wider viewing angle than most light-emitting displays. EPDs generally operate through the use of charged pigment particles that are held between a front substrate and a back substrate. When a voltage is applied across the two plates, the particles migrate to the plate that bears the opposite charge from that on the particles. Current EPD devices are limited in resolution and performance by usage of conventional materials. It would be desirable to infuse highly structured and surface-functionalized carbon particles to enhance EPD resolution, power consumption, and longevity while lowering production costs.

SUMMARY

This Summary is provided to introduce in a simplified form a selection of concepts that are further described below in the Detailed Description. This Summary is not intended to identify key features or essential features of the claimed subject matter, nor is it intended to limit the scope of the claimed subject matter. Moreover, the systems, methods, and devices of this disclosure each have several innovative aspects, no single one of which is solely responsible for the desirable attributes disclosed herein.

One innovative aspect of the subject matter described in this disclosure can be implemented as a three-dimensional (3D) carbon-based structure configured to guide a migration of electrically charged electrophoretic ink particles dispersed therein that are configured to be responsive to application of a voltage to the first electrode. The 3D carbon-based structure can include a plurality of 3D aggregates defined by a morphology of graphene nanoplatelets orthogonally fused together and cross-linked by a polymer, and a plurality of channels interspersed throughout the 3D carbon-based structure defined by the morphology. The plurality of channels can include a plurality of inter-particle pathways, and a plurality of intra-particle pathways. Each inter-particle pathway can include a smaller dimension than each inter-particle pathway. A second electrode can be disposed on the 3D carbon-based structure.

In some implementations, the electrophoretic display system can include a plurality of recesses formed in any one or more of the plurality of 3D aggregates or the plurality of channels. Any one or more inter-particle pathways can include an average radial dimension no greater than approximately 10 μm. Any one or more intra-particle pathways can include an average radial dimension greater than approximately 200 nm.

In some implementations, each 3D aggregate further comprises any one or more of graphene, carbon nano-onions, carbon nanoplatelets, or carbon nanotubes. The polymer can include any one or more of cellulose, cellulose acetate butyrate, styrene butadiene, polyurethane, polyetherurethane, acrylate, epoxy, or vinyl.

Another innovative aspect of the subject matter described in this disclosure can be implemented as a method of producing an electrophoretic display structure. The method can include self-nucleating a 3D open porous structure defined by a plurality of 3D carbon-based aggregates from a carbon-containing vapor flow stream; functionalizing one or more exposed surfaces of the 3D open porous structure with a nucleophilic moiety; and, cross-linking plurality of 3D carbon-based aggregates in the 3D open porous structure. The cross-linking can include converting the nucleophilic moiety; and, defining a porosity in the 3D open porous structure.

In some implementations, the self-nucleating of the 3D open porous structure further can include defining a porosity including an average pore size of greater than approximately 200 nm. The self-nucleating of the 3D open porous structure can include creating a plurality of pathways therein defined by the plurality of 3D carbon-based aggregates. The plurality of pathways can be configured to guide a plurality of charged mobile titania particles towards a charged electrode disposed on the electrophoretic display structure. Any one or more of the plurality of charged mobile titania particles can be configured to be non-reactively shuffled in or out of the 3D open porous structure.

Another innovative aspect of the subject matter described in this disclosure can be implemented as a display device including a pair of electrodes disposed on a substrate and a three-dimensional (3D) carbon-based structure disposed between the pair of electrodes. The 3D carbon-based structure can be configured to guide a migration of a plurality of electrically charged electrophoretic ink particles dispersed therein based on an application of a voltage differential to any one or more electrodes of the pair of electrodes. The 3D carbon-based structure can include a plurality of 3D aggregates defined by a morphology of graphene nanoplatelets orthogonally fused together and cross-linked by a polymer; and, a plurality of channels interspersed throughout the 3D carbon-based structure defined by the morphology. The plurality of channels can include a plurality of inter-particle pathways and a plurality of intra-particle pathways. Each inter-particle pathway can include a smaller dimension than each inter-particle pathway.

In some implementations, the 3D carbon-based structure can be independent of any one or more of Microcups or microcapsules. The plurality of electrically charged electrophoretic ink particles can include a plurality of negatively charged mobile titania particles. The negatively charged mobile titania particles can display a substantially white coloration. The negatively charged mobile titania particles displaying the substantially white coloration can be configured to be either attracted toward any one electrode of the pair of electrodes when that electrode is positively charged; or, repelled away from any one electrode of the pair of electrodes when that electrode is negatively charged.

In some implementations, the 3D carbon-based structure can be configured to be in a non-electrically conductive state. The display device can include an antenna configured to provide power to the display device. The display device can include a contrast layer between the 3D carbon-based structure and any one or more electrodes of the pair of electrodes. The contrast layer can be a first color. The plurality of electrically charged electrophoretic ink particles can be a second color that is different from the first color. The 3D carbon-based structure is defined by a polydispersity index of less than approximately 0.5.

Details of one or more implementations of the subject matter described in this disclosure are set forth in the accompanying drawings and the description below. Other features, aspects, and advantages will become apparent from the description, the drawings, and the claims. Note that the relative dimensions of the following figures may not be drawn to scale.

BRIEF DESCRIPTION OF THE DRAWINGS

Implementations of the subject matter disclosed herein are illustrated by way of example and are not intended to be limited by the figures of the accompanying drawings. Like numbers reference like elements throughout the drawings and specification. Note that the relative dimensions of the following figures may not be drawn to scale.

FIG. 15B shows a listing of features associated with a multi-layered electrophoretic display, in accordance with some implementations.

FIG. 16B shows an example implementation where two multi-layered substrates comprise different sets of components, in accordance with some implementations.

DETAILED DESCRIPTION

Introduction

Figure 1A:
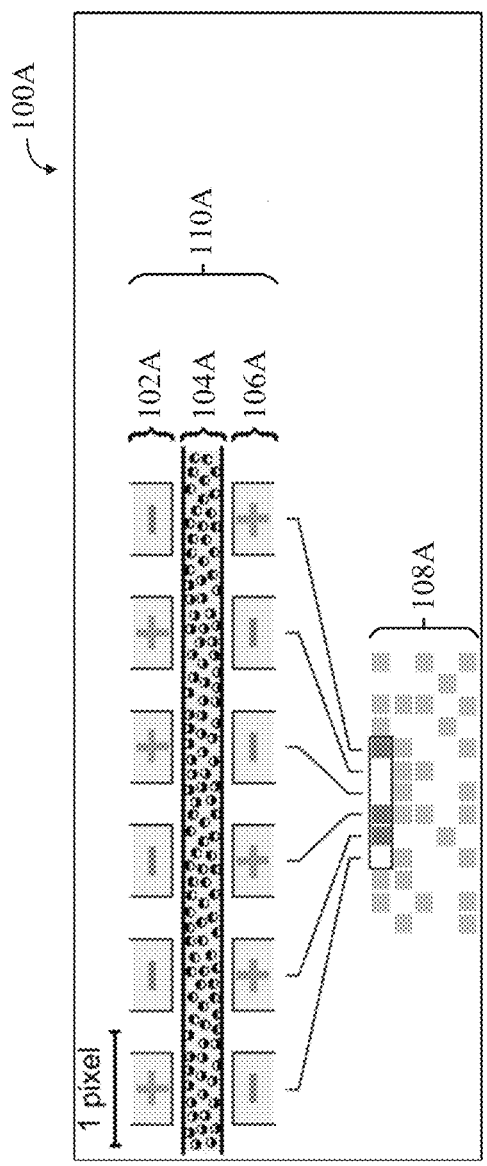
FIG. 1A shows a side cut-away schematic view 110A of an example conventional EPD device 100A, in accordance with some implementations.

Various implementations of the subject matter disclosed herein relate generally to systems and methods of manufacturing electrophoretic displays (referred to herein as "EPDs" and colloquially referred to as "electronic paper"). Electronic paper and e-paper, and also occasionally electronic ink, and electrophoretic displays are display devices (or constituent components or display devices) that essentially mimic the appearance of traditional ("ordinary") wet ink on as used on paper. However, unlike conventional backlit flat panel displays (referring to modern flat panel television and computer monitor displays) that emit light, electronic paper displays reflect light emitted onto it, similar to conventional paper. This may make EPDs relatively more natural to the eye and comfortable to read in a well-lit environment (such as outdoors during a sunny day, or in an office conference room), while also providing a wider viewing angle than most conventional or currently available light-emitting displays. Notably, available contrast ratios in EPDs have already reached levels similar to traditional print mediums, including newspaper. As a result, manufacturers now often can benchmark EPD performance based on whether they can be read in direct sunlight without generating images that appear to fade (referring to becoming visually indistinct or indistinguishable due to lack of sufficient contrast between light and dark surfaces in the presence of significant external illumination).

Some EPD technologies can retain static text and images indefinitely without electricity, thus providing a useful low-cost alternative to traditional digital displays for certain non-demanding application areas, such as signage for produce in a grocery store, or for disposable labeling on shipments and packages, etc. Flexible electronic paper can be configured to use plastic substrate materials and plastic electronics to provide structural rigidity in their respective display backplanes, while the lack of illumination can result in limited power consumption translating to low operational costs. Applications of EPDs are numerous and can include electronic shelf labels and digital signage, time tables at airports, bus, regional rail, and subway (train) stations, ride-share service pickup locations, electronic billboards (such as at sports arenas), smartphone displays, and portable electronic readers ("e-readers"), any one or more being able to display digital versions of books and magazines otherwise conventionally available in print medium form, with similar (or better) visual acuity and accuracy. Given that electronic devices and advances in cloud-based computing have dramatically increased the amount of data able to be processed and exchanged on a daily basis across a variety of economic sectors ranging from higher education to corporate finance, the ability to visually render up-to-date information to users has become increasingly important.

Of note, the detailed displaying of textual and graphical information is central to Internet of Things ("IoT") systems (referring to a system of interrelated computing devices, mechanical and digital machines provided with identifiers and the ability to transfer data over a network without requiring human-to-human or human-to-computer interaction), where low cost and power requirements have presented significant challenges regarding their widespread deployment and usage. Modern day display technologies, including organic light emitting diode (OLED) technology, provide brilliant, detailed, and high-resolution displays (complete with the ability to accurately replicate true black color representations), but these rich graphics often demand high operational costs as reflected in ongoing power consumption, and may otherwise not be particularly suitable for integration with self-powering or other alternative energy harvesting solutions. For many IoT applications, including electronic shelf or package labels, providing basic necessary information at low power is more desirable than a rich graphical experience at high power. Although more energy efficient electrophoretic display technologies have reduced ongoing energy requirements, they still often require high voltage and energy to drive the display, thus negating the possibility of using ambient energy collection approaches.

Unique 3D Hierarchical Open Porous Structure

The presently disclosed implementations provide EPD display devices with a carbon-containing layer positioned between oppositely charged electrode layers. The carbon-containing layer acts as a physical barrier for electrophoretic ink that migrates between the electrode layers to guide and control the migration for achieving high image resolution while maintaining low power consumption. The EPD devices present improvements beyond conventional EPD displays by incorporating three-dimensional (3D) carbon-based aggregates formed of graphene nanoplatelets in the carbon containing layer (where graphene nanoplatelets refer to a relatively new class of carbon nanoparticles and/or nanopowder) with multifunctional properties. Graphene nanoplatelets can consist of small stacks (3-5 layers, or up to 15 layers) of substantially vertically aligned graphene sheets having a platelet shape. Such graphene sheets can be nearly identical to those found in the walls of carbon nanotubes but presented in a planar form. Graphene nanoplatelets can replace carbon fiber, carbon nanotubes, nanoclays, or other compounds in many composite applications, including those applicable for the EPD devices presented herein.

The 3D carbon-based aggregates formed of graphene nanoplatelets can be synthesized (or otherwise "self-assembled", "self-nucleated", or created) in a controlled and tunable chemical reaction chamber or reactor upon flowing carbon-containing gaseous species therein, the gaseous species optionally including of one or more inert carrier gases, etc. The 3D carbon-based aggregates are innately self-grown in-flight at defined positions orthogonal (at a right angle) to one-another to define a 3D hierarchical open porous structure (the term "hierarchical" being used here to refer to multiple open pathways of various widths or other dimensions interspersed through or between larger 3D carbon aggregates). The disclosed self-growth or self-assembly process presents a significant procedural, synthetic, and technological departure from known and conventional carbon particle creation processes, such as annealing (referring to a heat treatment that alters the physical and sometimes chemical properties of a material to increase its ductility and reduce its hardness, making it more workable) and sintering (referring to the process of compacting and forming a solid mass of material by heat or pressure without melting it to the point of liquefaction) to present unexpected favorable material and performance properties in the 3D hierarchical open porous structure.

Regarding the specifics of the carbon-containing layer of the presented EPD devices, an organized and tunable porous arrangement is formed in the 3D hierarchical open porous structure that is configured to facilitate the electrophoretic migration of carbon-based electronic inks therein. The porous arrangement can be substantially immobile such that the 3D carbon-based aggregates are cross-linked and can be held in position by a binding material or binder to promote flexibility as may be desirable for formation of the porous arrangement on flexible substrates, such as paper, plastic, or other materials, yet still guide electrophoretic ink migration as desired. The electrophoretic carbon-based ink can be produced by using an ultrasonication method in which carbon materials are simultaneously fragmented and functionalized to make submicron ink particles ranging from approximately 100 nm to 200 nm that disperse effectively in a low dielectric solvent.

The presently disclosed EPD devices, related structures, and electrophoretic carbon-based inks can be 3D printed on flexible and disposable substrates, allowing for the development and economically feasible production of low-cost devices geared for everyday use. The EPD devices have relatively low power consumption requirements compared to traditional EPDs and can thus be run on relatively low amounts of power permitting for devices that can be operated by energy harvesting alone, rather than on (for example) portable battery power as occasionally found in conventional EPD devices. Applications for the disclosed devices are widespread, as discussed earlier, and include (at least), shipping labels for packages or price tags for store items, where the information to be displayed on the EPD can be conveyed wirelessly to the EPD. The low cost of the EPD allows for it to be discarded after the item upon which it is affixed has been delivered or purchased, etc.

Conventional Electrophoretic Display ("EPD") Devices

Dissimilar to conventional backlit flat panel displays that emit light, electronic paper displays, including the presently disclosed EPD devices, reflect light like traditional paper, making them natural for the human eye to observe and read, and can also provide for a wider viewing angle allowing for versatility in applications replacing traditional signage in retail stores, etc. And, many electronic paper technologies can hold (present) static text and images indefinitely without electricity, thus reducing ongoing power consumption requirements for applications in a variety of areas.

A side cut-away schematic view 110A of an example conventional EPD device 100A is shown in FIG. 1A, including an upper (transparent) electrode layer 102A, a liquid polymer layer containing electrophoretic ink capsules 104A, and a lower electrode layer 106A, along with a top-down view 108A of the EPD device 100A. In conventional practice, titanium dioxide ("titania") particles approximately one micrometer (μm) in diameter are dispersed in a hydrocarbon-based oil. A dark-colored dye can also be added to the oil, along with surfactants (referring to a substance which tends to reduce the surface tension of a liquid in which it is dissolved) and charging agents that cause the titania particles to take on an electric charge. This mixture is placed between two parallel, conductive plates (shown as upper and lower electrode layers 102A, and 106A, respectively) that are separated by a gap of 10 μm to 100 μm. When a voltage is applied across the two plates, the particles migrate electrophoretically (referring to the motion of dispersed particles relative to a fluid under the influence of a spatially uniform electric field) to the plate that bears the opposite charge from that on the particles. When the particles are located at the front (viewing) side of the display, the EPD 100A appears white, because the light is scattered back to the viewer by the titania particles due to their refractive index (a dimensional numerical value that describes how fast light travels through a given material). When the particles are located at the rear side of the display, that portion of the EPD appears dark, because the incident light is absorbed by the colored dye. If the rear electrode is divided into a number of small picture elements (pixels), then an image can be formed by applying an appropriate voltage to each region of the display to create a pattern of reflecting and absorbing regions.

Conventional EPDs can be configured to be controlled by or with metal oxide field effect transistor (MOSFET)-based thin-film transistor (TFT) technology. TFTs can be required to form a high-density image in an EPD. A common application for TFT-based EPDs are e-readers. EPDs are considered prime examples of the electronic paper category, because of their paper-like appearance and low power consumption. Examples of commercial electrophoretic displays include the high-resolution active matrix displays used in the Amazon Kindle, Barnes & Noble Nook, Sony Reader, and Kobo eReader.

Figure 1B:
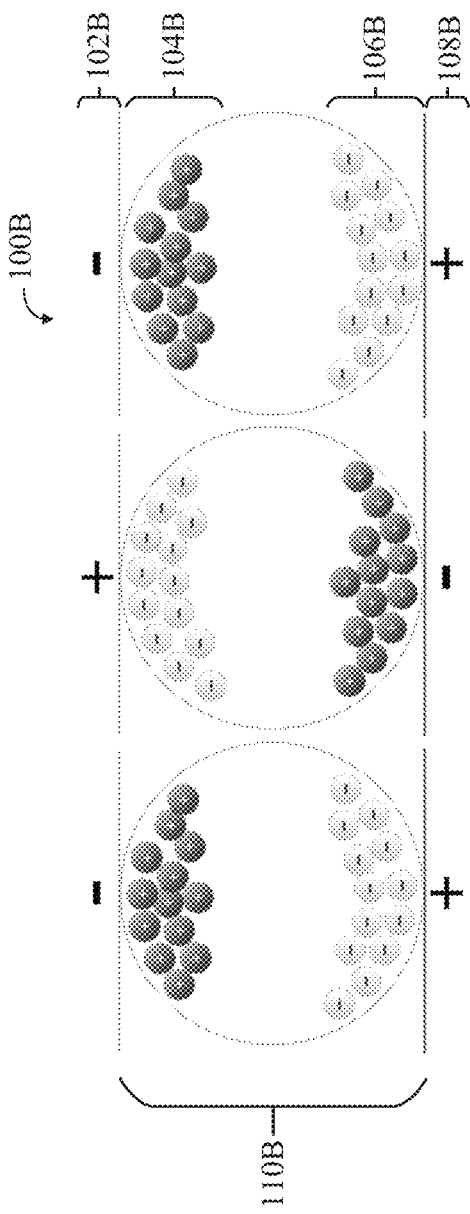
FIG. 1B shows a conventional microencapsulated electrophoretic display, in accordance with some implementations.

A conventional microencapsulated electrophoretic display 100B is shown in FIG. 1B and includes a top and bottom electrode array, 102B and 108B, respectively, having an alternating and opposite polarity or charge as shown, along with white-colored negatively charged particles 104B and black-colored dye 106B (collectively referred to as electronic ink). The EPD holds microcapsules in a layer of liquid polymer, sandwiched between two arrays of electrodes 102B and 108B, the upper of which is transparent. The two arrays of electrodes 102B and 108B are aligned to divide the sheet into pixels, and each pixel corresponds to a pair of electrodes situated on either side of the sheet. The sheet is laminated with transparent plastic for protection, resulting in an overall thickness of 80 micrometers, or twice that of ordinary paper. The network of electrode arrays (referring to the two arrays of electrodes 102B and 108B) connects to display circuitry, which turns the electronic ink "on" and "off" at specific pixels by applying a voltage to specific electrode pairs. A negative charge to the surface electrode repels the white-colored negatively charged particles 106B to the bottom of local capsules, forcing the black-colored dye 106B to the surface to turn the pixel black. Reversing the voltage has the opposite effect. It attracts the white-colored negatively charged particles 106B to the surface, turning the pixel white.

Ultra-Thin, Plastic Passive Matrix EPD Displays (PMEPDs)

Figure 1C:
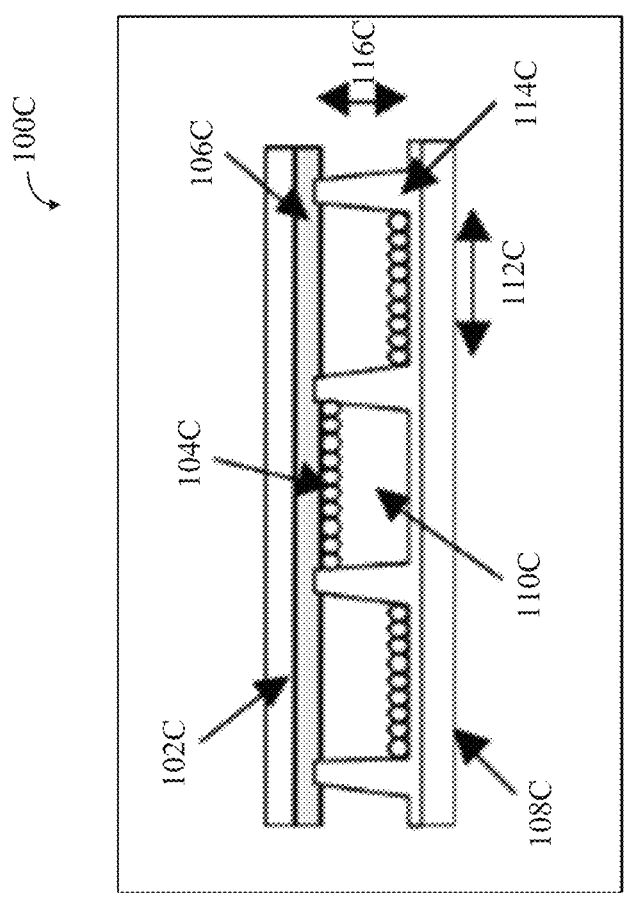
FIG. 1C shows a conventional PMEPD 100C using Microcup technology, in accordance with some implementations.

A conventional PMEPD 100C using Microcup technology is shown in FIG. 1C and includes a top patterned conductor film 102C, charged particles 104C, a sealing or adhesive layer 106C, bottom patterned conductor film 108C, and a dielectric solvent 110C. An example Microcup 114C (which may also or alternatively refer to a plurality of Microcups as Microcups 114C) can have a cup dimension 112C, referring to a width (w) or a length (l), ranging from 60-180 μm, and a Microcup height 116C of 15-40 μm. The top patterned conductor film 102C and bottom patterned conductor film 108C sandwich the one or more Microcups, each of which is filled with the dielectric solvent 110C, permitting for guided migration of charged particles 104C pursuant to the formation of Microcups 114C upon exposure to voltage.

PMEPDs have been prepared by a format flexible, roll-to-roll manufacturing process based on Microcup and sealing technologies. High switching rate Microcup PMEPDs having threshold voltages ranging from 5 to 50V with a sharp electro-optical transition ("gamma") have been demonstrated in conventional products and technologies. A PMEPD using the traditional column and row electrode pattern has often provided a significant technical challenge due to the lack of inherent threshold characteristics to suppress or eliminate undesirable crosstalk or cross-bias among adjacent pixels during matrix driving.

Several attempts have been made to address the threshold issue. For example, an additional conductive layer or grid electrode have been employed to suppress the undesirable particle movement in non-addressing pixels. Such PMEPDs have been developed, but typically require high manufacturing cost due to the requisite multilayer electrode structures (which have a high cost themselves). Alternatively, magnetic particles and a magnetic electrode have been proposed to provide the required threshold, again at the expense of manufacturing cost. An electrophoretic fluid having inherent threshold characteristics has been reported, but with tradeoffs in for examples, response time, operation voltage, brightness, image uniformity, and display longevity.

As shown in FIG. 1C, walls or partitions of the Microcups 114C provide mechanical support throughout the entire EPD and can provide favorable physico-mechanical properties including scratch, impact, and flexure resistances. They also enable color separation by effectively isolating fluids of different properties such as colors and/or switching rate in each individual cup. With continuous filling and sealing technologies, EPDs may be manufactured roll-to-roll at a high speed at a relatively low cost.

Limitations Found in Conventional Technology

Although often at a lower cost to produce and operate due to their relative simplicity in comparison to other types of modern flat-panel display devices, electronic paper technologies can provide a very low refresh rate (which is undesirable) compared to other display technologies, such as liquid crystal displays (LCDs). This shortcoming prevents producers from implementing sophisticated modern interactive applications (using, for example, fast-moving menus, mouse pointers or scrolling) like those common on standard mobile devices (such as smartphones). An example of this limit during usage is that a document on a conventional EPD device might not be smoothly zoomed without:

(1) extreme blurring during the transition; or,
(2) a very slow zoom (both being highly undesirable).

Another limit is that a shadow of an image may be visible after refreshing parts of the screen, leaving an undesirable residue that visually interferes with subsequent imagery displayed on the screen. Such shadows are a severe nuisance and are termed "ghost images" in industry, and the effect is termed "ghosting". This effect is reminiscent of screen burn-in but, unlike screen burn-in, can be resolved after the screen is refreshed several times.

Figure 1D:
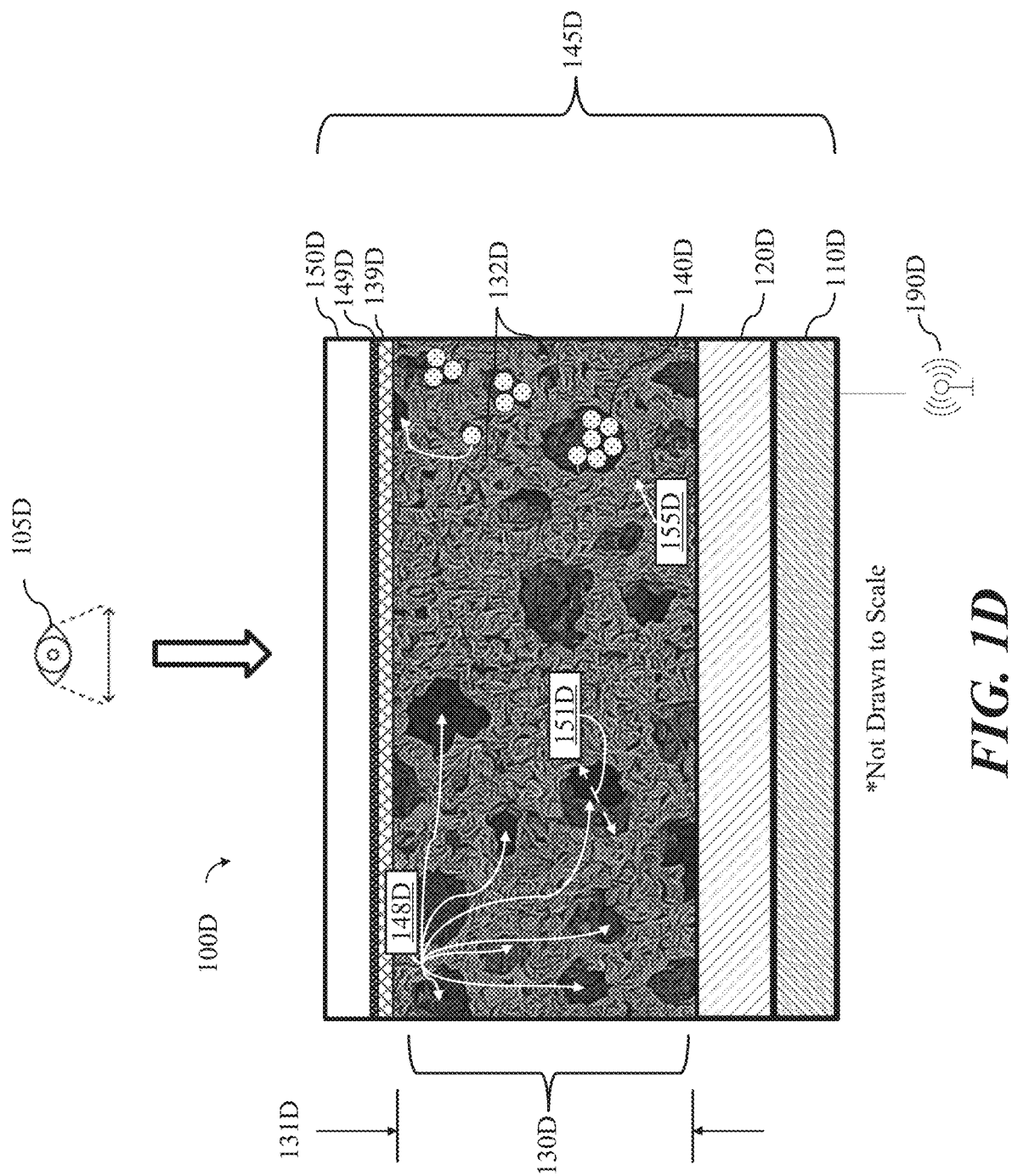
FIG. 1D shows a cross-sectional schematic diagram of an EPD device that includes a structure that is carbon-based, in accordance with some implementations.

Novel EPD Devices Including a 3D Hierarchical Open Porous Structure Acting as a Stationary Phase Through which Particles can Migrate Seeking to address limitations encountered in conventional EPD device technology, FIG. 1D shows a cross-sectional schematic diagram of an EPD device 100D that includes a structure 130D that is carbon-based, three-dimensional (3D), and includes tuned openings or pathways that are "hierarchical" in nature, such as by being organized by opening or pathway width. Accordingly, the structure 130D is generally open and porous. In the configuration shown in FIG. 1D, the EPD device 100D includes multiple layers 145D that are deposited on a substrate 110D through any one or more known methods, and by using commercially available tools.

As shown in FIG. 1D, the EPD device 100D includes a first electrode layer 120D disposed on the substrate 110D, the structure 130D disposed on the first electrode layer 120D, and a plurality of charged electrophoretic ink capsules 140D interspersed within and around a porous arrangement 148D formed in the structure 130D, and a second electrode layer 150D disposed thereon. The structure 130D can be sealed with an isolating sealing layer 139D and laminated to the second electrode 150D using an optically clear (transparent) adhesive material 149D. The plurality of charged electrophoretic ink capsules 140D electrophoretically migrates (referring to the motion of dispersed particles relative to a fluid under the influence of a spatially uniform electric field) toward layer 150D (relative to the charge of the particles and that of that section of the layer, substantially as introduced earlier for conventional EPD devices in FIGS. 1A-1C, where charged electrophoretic ink capsules 140D (that may be white-colored and negatively charged) would be attracted to a positively charged first electrode 102B) through the structure 130D to create high-resolution images (such as, patterns, graphics, text) to be viewed from layer 150D, as indicated by the icon of an eye 105D, and substantially replicate the appearance of traditional ink on paper.

Generally, the structure 130D forms a stationary solid phase between the first and second electrode layers, 120D and 150D, respectively, and can include porous carbon materials that are networked together with each other. Titanium dioxide (interchangeably referred to herein as "titania", "titanium IV oxide", refers to the naturally occurring oxide of titanium with the chemical formula of $TiO_2$)-inclusive electrophoretic ink particles (of a contrasting color to the stationary carbon solid phase) migrate pursuant to the application of a voltage to any one or more of the first and second electrode layers, 120D and 150D, respectively. In operation, negatively charged mobile titania particles can be attracted towards a positively charged first electrode layer 120D to display white coloration or repelled away from a negatively charged first electrode layer 120D to result in the display of black (or darker than white) coloration. Any one or more of the mobile titania can be guided or shuffled in and out (non-reactively) by the structure 130D (also referred to as a stationary solid phase). Such an approach can be easily distinguished from conventional techniques relying on electrophoretic inks dispersed in a dielectric solvent that trapped or at least substantially confined in either Microcups or microcapsules, with movement limited to the organization and placement of any the Microcups or microcapsules, respectively.

Fabrication of a Carbon-Based 3D Hierarchical Open Porous Structure

Conventional EPD devices can be manufactured by roll-to-roll formal flexible manufacturing processes and can include charged titania and/or ink particles dispersed in a dielectric solvent within Microcups through which charged particles migrate to form and show images. EPD devices can include a hydrocarbon oil positioned between adjacent electrode layers, where charged particles migrate through that oil to form images. EPD devices can further include carbon configurations prepared by annealing or sintering techniques as discussed earlier, both of which are conventional and known techniques and can fail to provide the fidelity required to achieve the structure 130D as shown and discussed in FIG. 1D.

Unlike the discussed (or other) conventional technologies, the structure 130D can be nucleated and grown in an atmospheric plasma-based vapor flow stream of reagent gaseous species, which include methane ($CH_4$), to self-form an initial carbon-containing and/or carbon-based particle (without otherwise requiring dedicated seed particle). That initial particle may be expanded by forming multiple orthogonally interconnected aggregates 132D, each aggregate 132D being of at least 400 nm in diameter, such as 400 nm to 20 µm, or such as an average diameter of 1 µm to 20 µm, where each aggregate contains multiple graphene nanoplatelets.

The initial particle then expands by being:
  synthesized "in-flight", describing the systematic coalescence (referring to nucleation and/or growth from an initial carbon-based homogenous nucleation independent of a seed particle) of additional carbon-based material derived from incoming carbon-containing gas mid-air within a microwave-plasma reaction chamber; and/or,
  deposited or grown (alternatively referred to as "self-nucleated") directly onto a supporting or sacrificial substrate, such as a current collector, within a thermal reactor; and/or exposed to one or more post-processing operations to achieve particular desirable properties.

Coalescence refers to a process in which two phase domains of the same composition come together and form a larger phase domain. Alternatively put, the process by which two or more separate masses of miscible substances (carbon derivatives formed from the flowed methane gas) appear to "pull" each other together should they make the slightest contact.

Accordingly, the structure 130D forms a display architecture where carbon-based materials are uniquely self-nucleated to synthesize or otherwise produce a tunable porous (non-electrically conductive) network positioned between the first and second electrode layers, 120D and 150D, respectively, that can guide migratory movement of particles therein and therefore produce and reproduce sharp high-quality imagery not otherwise achievable through conventional means.

Returning to synthetic procedures for creating the structure 130, as introduced above, the vapor flow stream including carbon-containing constituent species, such as methane ($CH_4$) may be flowed into one of two general reactor types:
- a thermal reactor; or,
- a microwave-based (and/or "microwave") reactor. Suitable types of microwave reactors are disclosed by Stowell, et al., "Microwave Chemical Processing Reactor", U.S. Pat. No. 9,767,992 (Sep. 19, 2017), incorporated herein by reference in its entirety.

The term "in-flight", as used herein, refers to a novel method of chemical synthesis based on contacting particulate material derived from inflowing carbon-containing gaseous species, such as those containing methane ($CH_4$), to "crack" such gaseous species. "Cracking", as generally understood and as referred to herein, implies the technical process of methane pyrolysis to yield elemental carbon (such as high-quality carbon black) and hydrogen gas, without potential problematic contamination by carbon monoxide, and with virtually no carbon dioxide emissions. A representative endothermic hydrocarbon cracking reaction that can occur within the microwave reactor as so described above is shown as equation (1) below:

$$CH_4 + 74.85 \text{ kJ/mol} \rightarrow C + 2H_2 \qquad (1)$$

Carbon derived from the above-described "cracking" process can fuse (self-bind) together while being dispersed in a gaseous phase, referred to as "in-flight", to create carbon-based particles, structures, (substantially) 2D graphene sheets, and the aggregates 132D derived therefrom. The aggregates 132D (collectively which define the structure 130D) can each individually include (or consist of) multiple layers of graphene nanoplatelets fused together, each layer of graphene nanoplatelets being fused at an angle orthogonal to adjacent graphene nanoplatelets, to serve as a type of intrinsic, self-supporting scaffold that can also be structurally supplemented by traditional chemical (wet), binders or other joining materials allowing for retention of favorable structural characteristics of the structure 130D even in circumstances of flexure or other movement of the second electrode layer 120D and/or the substrate 110D.

Electrical conductivity of deposited carbon and/or carbon-based materials used for creating the structure 130D can be tuned (or eliminated) by adding metal additions into the carbon phase in a first part of a deposition phase or to vary the ratios of various carbon particles derived from cracking hydrocarbon gases as discussed. Other parameters and/or additions may be adjusted, as a part of an energetic deposition process, such that the degree of energy of deposited carbon and/or carbon-based particles will either: (1) bind together; or, (2) not bind together. And, by nucleating and/or growing the structure 130D in an atmospheric plasma-based vapor flow stream either "in-flight" or directly onto a supporting or sacrificial substrate, a number of the operations and components found in both EPD devices and EPD device-making processes can be reduced or eliminated entirely. Also, tailoring and tunability can be enabled or added into the discussed carbons and/or carbon-based materials.

Dimensions of Pores of the Carbon-Based 3D Hierarchical Open Porous Structure

The carbon structure 130D can be synthesized in-flight, as described above, with a 3D hierarchical structure comprising short range, local nano-structuring in combination with long range approximate fractal feature structuring, which in this context refers to the formation of successive layers involving the 90-degree rotation of each successive layer relative to the one beneath it, and so on and so forth, allowing for the creation of vertical (or substantially vertical) layers and/or intermediate ("inter") layers. Such an orientation is referred to herein as "orthogonal layering" or "orthogonal interconnection" to create the structure 130D with the porous arrangement 148D formed therein. To achieve desired EPD performance qualities, the porous arrangement 148D can be tuned to include:
- inter-particle pores 151D that are void spaces, cavities or openings within and around aggregates 132D that extend between mesoporous and macroporous dimensions (defined by the International Union of Pure and Applied Chemistry, IUPAC, as having pore diameters extending from 2 nm and 50 nm and greater than 50 nm, respectively) and are sized from 200 nm to 2 μm, 400 nm to 5 μm, or up to 10 μm, referring to the average distance between sections of the self-assembled aggregates 132D forming the structure 130D; and
- intra-particle porosity 155D is defined as being between materials within each aggregate 132D, such as between layers of graphene, and may have an average pore size of 200 nm to 2 μm.

The structure 130D can include aggregates 132D interconnected by polymers (such as a cross-linked polymer).

The substrate 110D can be a flexible material such as a polymer film or a paper-based material, as well as being relatively low-cost and disposable, being particularly well-suited for single use applications. Example materials suitable for usage to form the substrate 110D include any one or more of cardboard, paper, polymer-coated paper, and polymer films, as well as card stock, labels, and boxes. Alternative configurations of the EPD 100 are possible enabling extended use periods due to the dormant, non-power consumptive nature of the EPD 100D when not activated.

Functionality of the Electrophoretic Display (EPD) Device

Any one or more of first and second electrode layers 120D or 150D can incorporate an electrical conductor used to make contact with a nonmetallic part of a circuit (such as a semiconductor, an electrolyte, a vacuum or air) and generate an electric field for various components (such as pixels) of the EPD device 100D. The first and second electrode layers 120D and 150D, respectively, can be made from identical, similar, or different materials relative to each other. In some implementations, the first and second electrode layers 120D and 150D, respectively, can each include a plurality of individual electrodes positioned substantially adjacent to each other, with any one or more of the individual electrodes printed by a conductive ink. Potential formative materials used to fabricate electrode layers 120D and 150D can include indium tin oxide (ITO). The second electrode layer 150D is at least substantially transparent to allow viewing of images created by migration of the plurality of charged electrophoretic ink capsules 140D as guided by the structure 130D. The second electrode layer 150D can be an ITO-coated film such as polyethylene terephthalate (PET), while the first electrode layer 120D can be made from a carbon-inclusive material, such as graphene or metal-functionalized carbon allotropes (including graphene). Carbon particles prevalent in the first electrode layer 120D can be interconnected by a binder, such as a polymer, including, cellulose, cellulose acetate butyrate, styrene butadiene, polyurethane, polyether-urethane, or cross-linkable resins.

The structure 130D can be initially synthesized without requiring a nucleation (alternatively referred to as a "seed" particle), but later can be exposed to one or more post-processing operations to enable highly sensitive tuning (regarding width, length, or any other dimension) of any one or more porous pathways of the porous arrangement 148D, while remaining entirely non-conductive overall. Carbons and carbon-based materials can be post-processed (as further described in at least FIG. 4B) to make the porous arrangement 148D such that electrophoretic particles can, without impediment, move in and out of the structure 130 through porous arrangement 148D. The unique morphology of carbons used to produce the structure 130 guide migrating particles without creating, facilitating or in any way conducting electricity and/or electric current. In essence, the structure 130 is entirely non-conductive since one or more processes employed to form cross-linked carbons (as detailed in FIG. 4B of the structure 130) yield non-conductive materials.

Accordingly, the pores 151D between carbon particles 132D can enable the plurality of charged electrophoretic ink capsules 140D to electrophoretically migrate (referring to the motion of dispersed particles relative to a fluid under the influence of a spatially uniform electric field) through the structure 130D solely or at least primarily in response to activation and/or deactivation of any one or more of the first and second electrode layers 120D and 150D, respectively without experiencing unwanted electrical interference from the structure 130D itself. For instance, charged ink capsules of the plurality of charged (generally white or light colored) electrophoretic ink capsules 140D electrophoretically can migrate toward second electrode layer 150D by being guided by the structure 130D to form a detailed visible image at resolution levels not otherwise possible with conventional technologies lacking the unique particle guiding capabilities of the structure 130. In some configurations, most or all of the plurality of charged electrophoretic ink capsules 140D can be lighter-colored to contrast darker colors of the structure 130D.

Most or all of the plurality of charged electrophoretic ink capsules 140D can be titanium dioxide (titania) or other white colloidal particles on the order of 100 nm that are dispersed in a low dielectric solvent such as any one or more of isoparaffinic hydrocarbons, such as Isopar-L and Isopar-G, xylene, 1,2-dichlorobenzene, tetralin, diethylbenzene, toluene, decane, dodecane, hexadecane, cyclohexane, 2-phenylhexane, 1-phenylheptane, 1-phenyldecane, tetrachloroethylene. The plurality of charged electrophoretic ink capsules 140D can be configured to include a charge control agent (CCA), such as aerosol sodium di-2-ethylhexylsulfo-succinate (AOT), poly(isobutylene succinimide) (PIBS), or sorbitan oleate (SPAN®) to have a defined polarity so that they move in response to voltage differentials applied to any one or more of the first and second electrode layers 120D and 150D, respectively.

To better maintain a defined overall structural shape or pattern during circumstances of flexure of the substrate 110D, the structure 130D can include aggregates 132D interconnected with each other by a binder such as a polymer including cellulose, cellulose acetate butyrate, styrene butadiene, polyurethane, polyether-urethane or cross-linkable resins such as, acrylates, epoxies, vinyls that form polymerizable covalent bonds. The binder links the aggregates 132D together but does not consume or otherwise fill up the pores 151D and/or other voids, spaces, or gaps encountered between the aggregates 132D that are interconnected with each other to form the structure 130D.

In some implementations, the aggregates 132D can include constituent formative elements including carbon allotropes such as graphene, carbon nano-onions (CNOs), carbon nanotubes (CNTs), or any combination thereof, such that, in some implementations, the structure 130D can include graphene at defined weight and/or volume percentages, including greater than 50%, greater than 80%, or greater than 90%. A thickness 131D of the structure 130D can be made thinner than conventional EPD materials due to the conductive nature of the structure 130D, which enables electrode connections therein.

Fabricating the structure 130D as a thin layer can result in circumstances where less energy is required to move plurality of charged electrophoretic ink capsules 140D, therefore making the EPD device 100D more conducive to being powered solely by energy harvesting methods such as an energy harvesting antenna 190D, or others disclosed by Stowell, et al., in U.S. patent application Ser. No. 16/282, 895 entitled "Antenna with Frequency-Selective Elements" filed on Feb. 22, 2019, incorporated herein in its entirety. For example, the thickness 131D of the structure 130D can be configured to be approximately 10 µm to approximately 40 µm, or approximately 10 µm to approximately 100 µm. The electrical conductivity of the structure 130D can be greater than 20,000 S/m, or greater than 5,000 S/m, or greater than 500 S/m, or greater than 50 S/m. Defined in terms of resistance, the sheet resistance of the structure 130D may be less than 1 Ohm/sq., or less than 10 Ohm/sq., or less than 100 Ohm/sq., or less than 1,000 Ohm/sq.

Figure 1E:
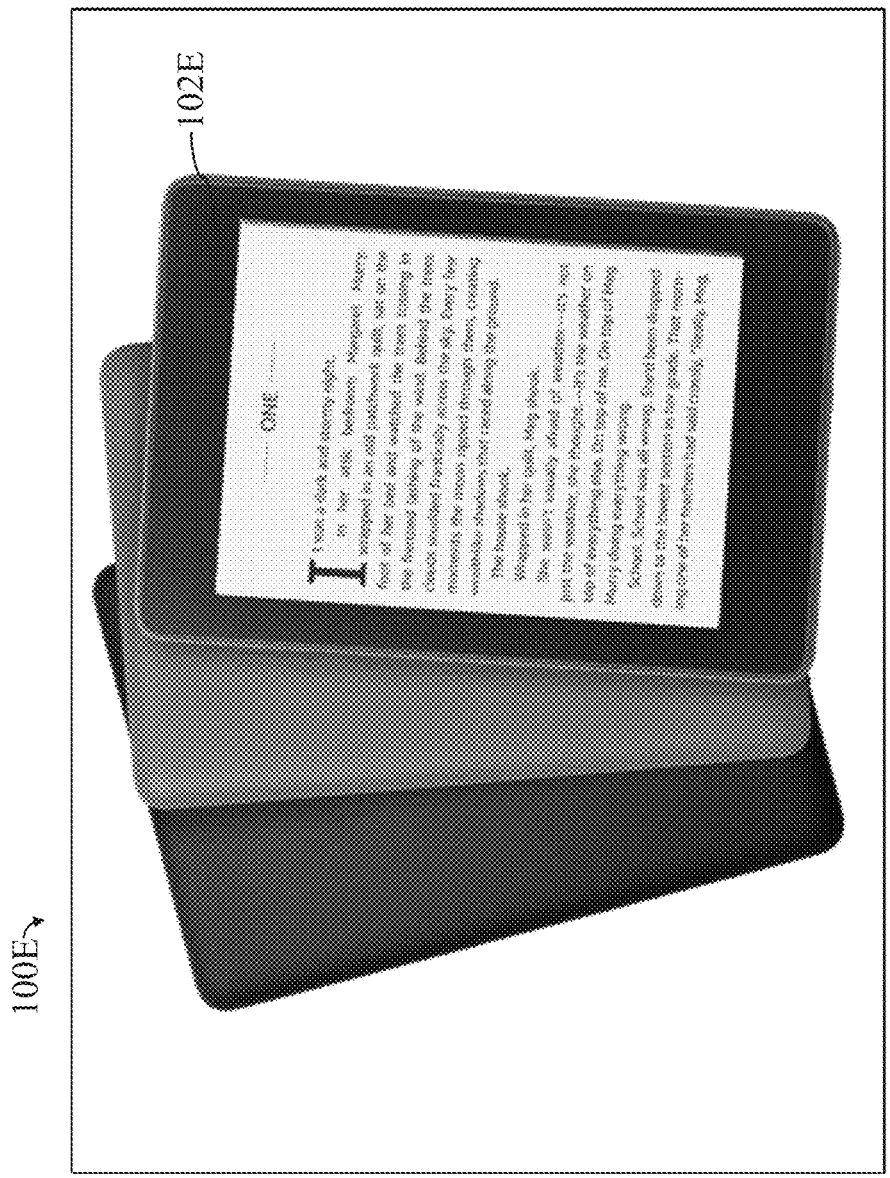
FIG. 1E shows an example EPD device that include carbon-inclusive structures, in accordance with some implementations.

FIG. 1E shows an example EPD device 100E that can include the EPD device 100D with the structure 130D, both shown and discussed in FIG. 1D. The example EPD device 100E can generate high-resolution text 102E and drawings able to be viewed from wide angle, thereby enhancing the desirability of the EPD device 100E.

Figure 2:
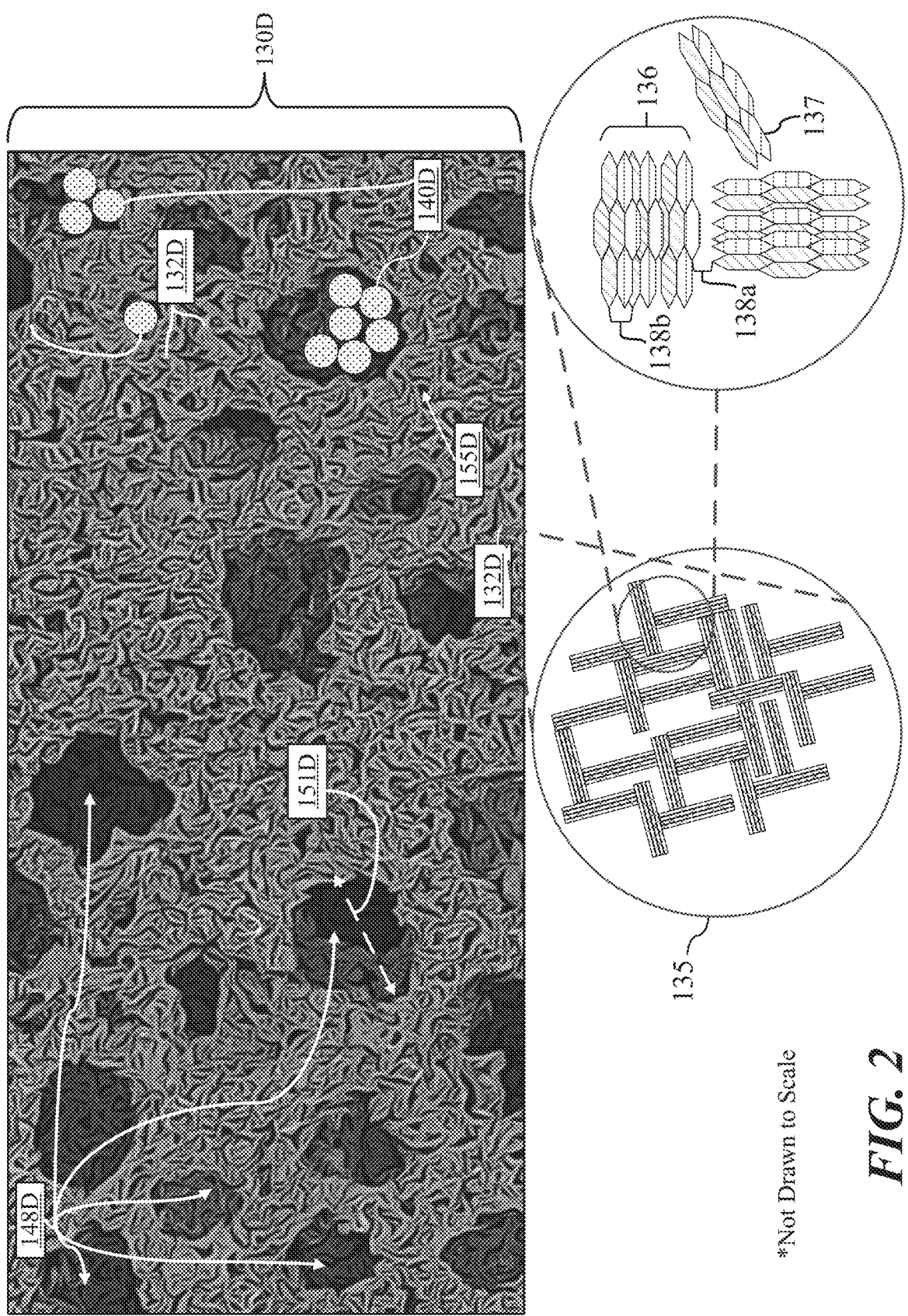
FIG. 2 shows a schematic diagram illustrating a structure for an electrophoretic display (such as that shown in FIG. 1), in accordance with some implementations.

FIG. 2A shows an enlarged view the structure 130D (shown in FIG. 1D) for the EPD display 100D, in accordance with some implementations. As indicated earlier in FIG. 1D, the porous arrangement 148D can be tuned to include:

- inter-particle pores 151D that are void spaces, cavities or openings within and around aggregates 132D that are sized from 200 nm to 2 µm, 400 nm to 5 µm, or up to 10 µm, referring to the average distance between sections of the self-assembled aggregates 132D forming the structure 130D; and
- intra-particle porosity 155D is defined as being between materials within each aggregate 132D, such as between layers of graphene, and may have an average pore size of 200 nm to 2 µm.

The aggregates 132D themselves can be of sized to be at least approximately 400 nm in diameter, such as approximately 400 nm to approximately 20 µm, or such as an average diameter of approximately 1 µm to approximately 20 µm, and be cross-linked together (orthogonally) by a polymer. Detailed view 135 shown in FIG. 2B depicts an enlarged schematic representation of an example aggregate 132D including organized graphene nanoplatelets orthogonally fused together, each nanoplatelet possibly including few layer graphene (FLG) 136 and single-layer graphene 137. Representative inter-particle porosity 138*a*, shown in FIG. 2C (a further enlargement of that shown in FIG. 2B), is between FLG 136 (also, in some implementations, FLG 136 can be the aggregates 132B), whereas intra-particle porosity 138*b* is within any one or more FLG 136, such as between individual graphene layers of graphene and be sized at approximately 200 nm to approximately 2 µm.

Figure 3A:
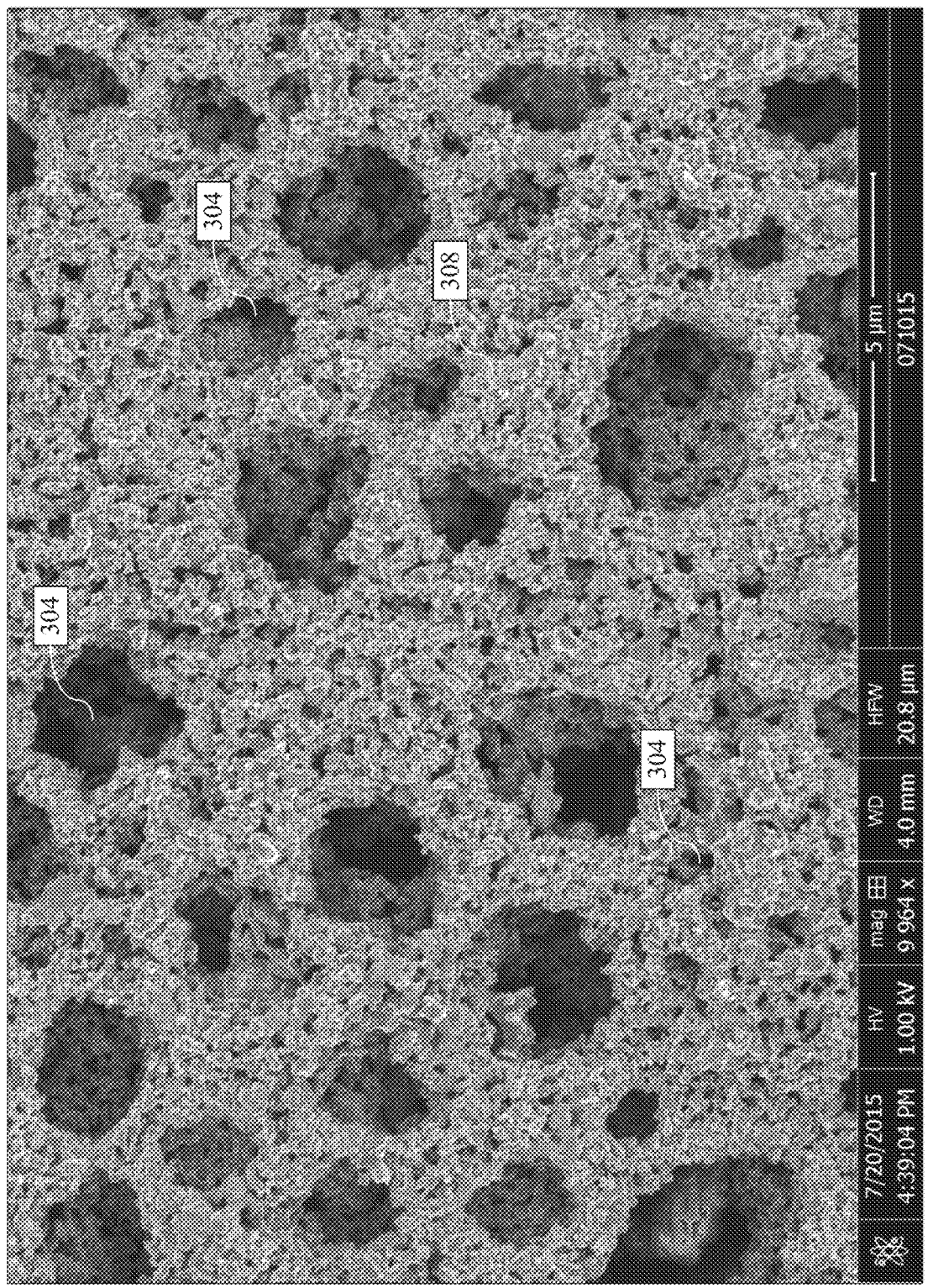
FIG. 3A-3B show scanning electron micrograph images of a structure (such as that shown in FIG. 2), in accordance with some implementations.
Figure 3B:
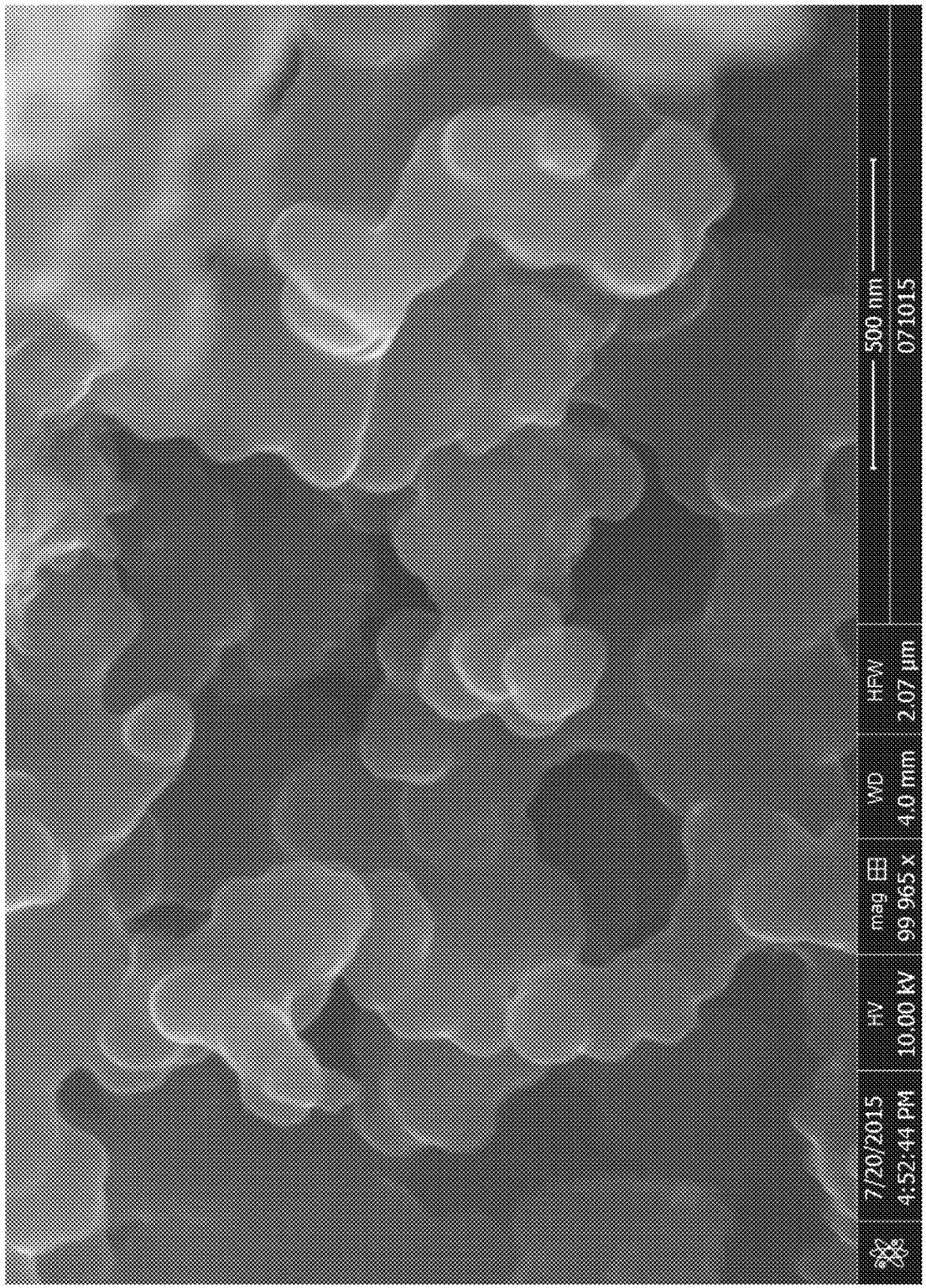

FIGS. 3A and 3B are scanning electron microscope (SEM) micrographs of a carbon network 300 and a carbon network 301 (any one or more of which is representative of the structure 130D shown in FIG. 1D), respectively, where the carbon networks 300 and 301 consist of carbon-based materials only (such as the aggregates 132D grown "in-flight" in an atmospheric vapor stream of a carbon-containing gaseous species, such as methane, as discussed earlier with relation to FIG. 1D), without application or usage of resin to connect the aggregates 132D. FIG. 3A shows the carbon network 300 including various larger inter-particle pores 304 (sized from 200 nm to 2 µm, 400 nm to 5 µm, or up to 10 µm) of varying sizes and smaller intra-particle pores 308 (having an average pore size of 200 nm to 2 µm) that are shown by the highly textured 3D construction of the carbon network 300 shown in FIG. 3A. FIG. 3B is a higher magnification micrograph of the carbon network 300 shown in FIG. 3A illustrating porosity of the carbon network 301. The carbon networks 300 and 301 illustrate example carbon-based porous structures without the usage of resin materials to bind carbon materials together. In certain usage or flexure conditions, the carbon networks 300 and 301 can fracture and disintegrate, thus failing to provide a guide for migrating electrophoretic ink particles to form high-resolution images, thus limiting their ability to be applied electrophoretic displays, such as the EPD device 100 shown FIG. 1. To address such potential performance issues, resins (referring to a solid or highly viscous substance of plant or synthetic origin that is typically convertible into polymers) can be systematically incorporated into any one or more of the carbon networks 300 and 301 for strengthening and maintenance of structure purposes, enabling them to be used in EPD devices without encountering breakage or other performance issues.

Figure 4A:
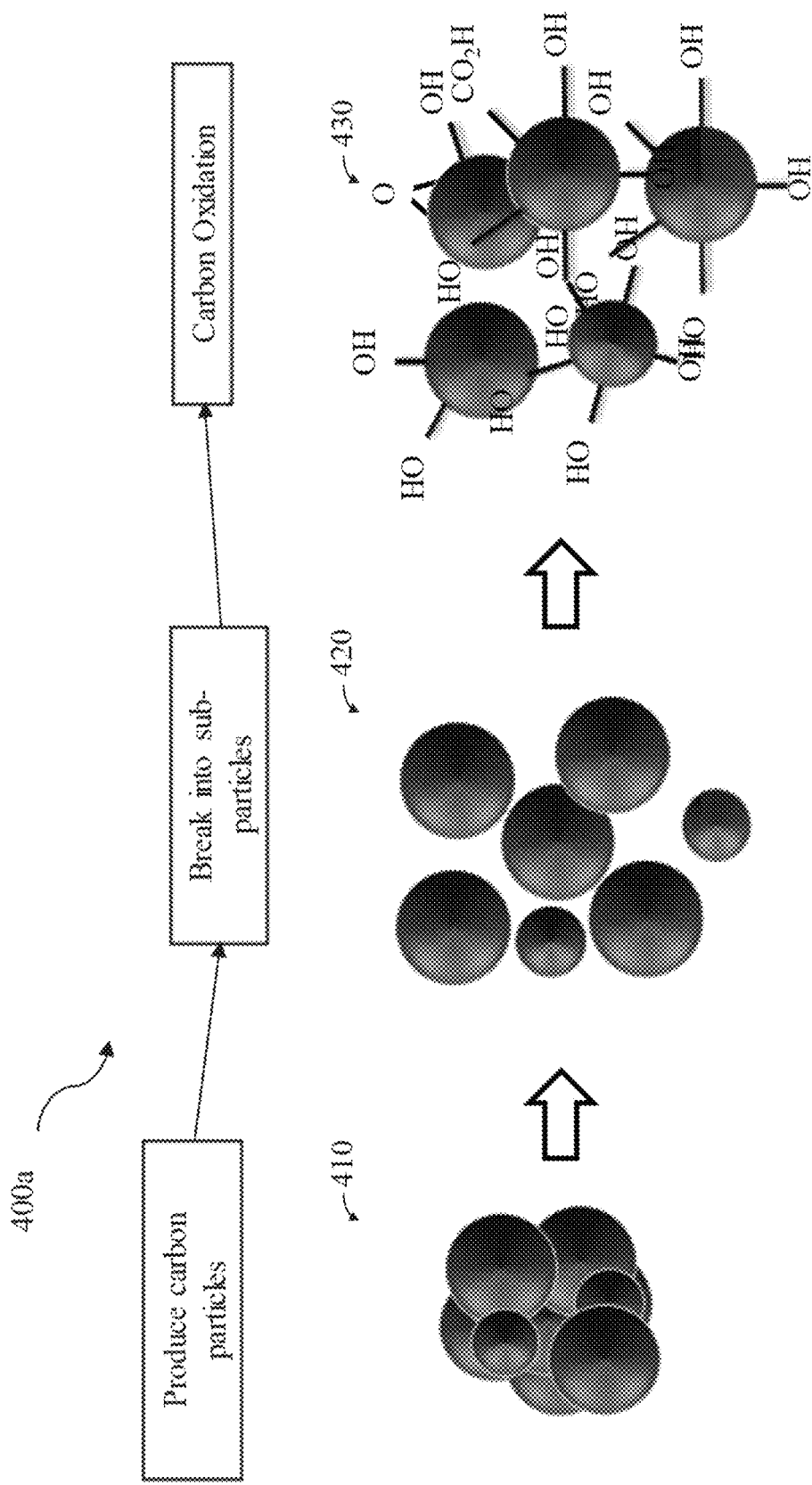
FIGS. 4A-4B are schematic diagrams representing methods for making a structure (such as that shown in FIG. 2) for the electrophoretic visual display (such as that shown in FIG. 1), in accordance with some implementations.
Figure 4B:
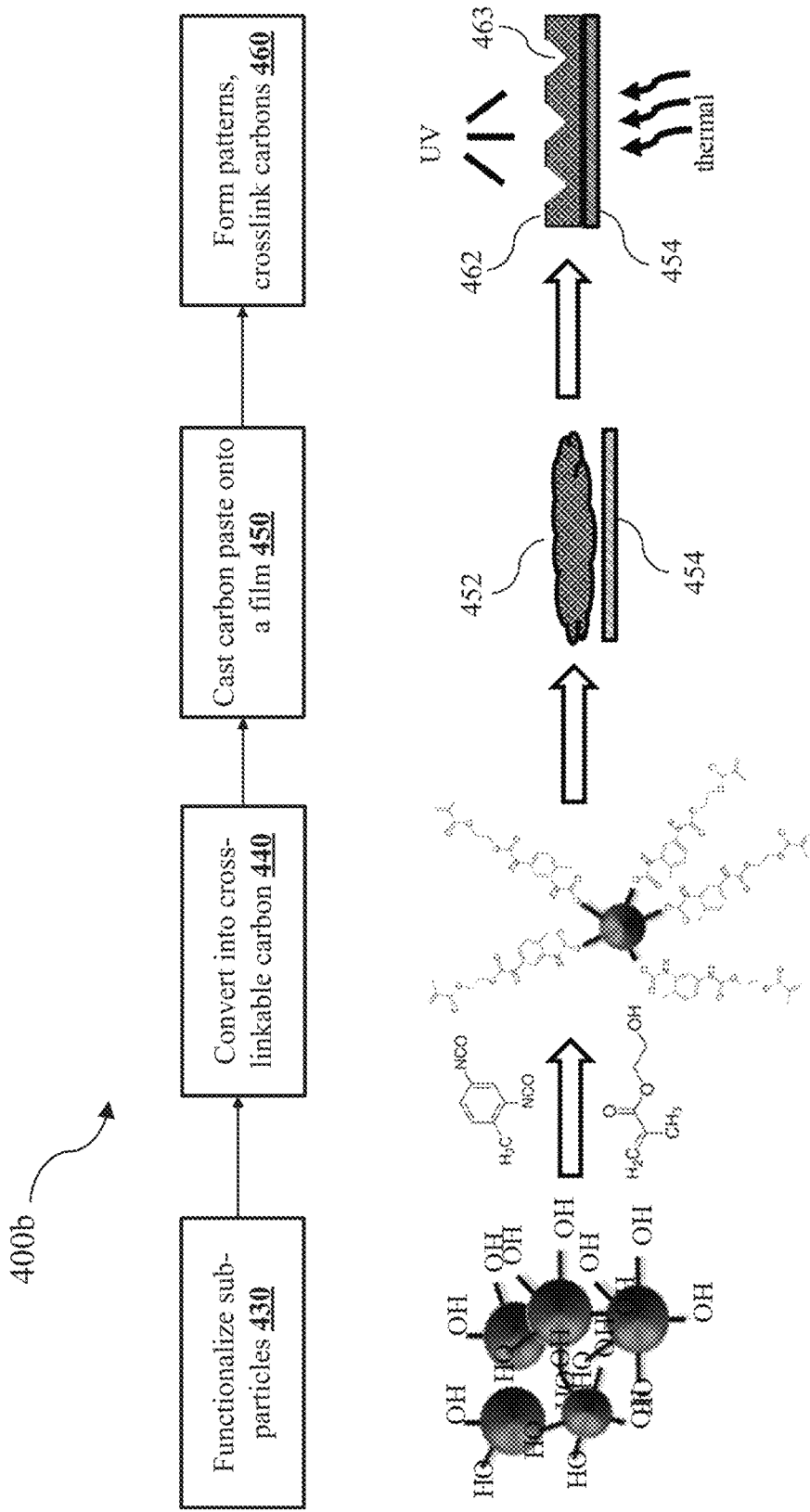

FIGS. 4A and 4B show flowcharts with accompanying explanatory schematic diagrams 400*a* and 400*b* both related to fabricating carbon-based scaffold or structures, such as structure 130D shown in 1D as well as carbon networks 300 and 301 shown in FIGS. 3A and 3B respectively, any one or more suitable for incorporation with electrophoretic displays, such as EPD device 100D shown in FIG. 1D. The diagram 400*b* shown in FIG. 4B represents a continuations of the diagram 400*a* shown in FIG. 4A. In operation 410 of FIG. 4A, carbon particles, such as the aggregates 132D shown in FIG. 1D, can be grown "in-flight" in a substantially atmospheric vapor flow stream as described earlier and/or using the microwave plasma reactors and/or methods described in U.S. Pat. No. 9,812,295, entitled "Microwave Chemical Processing," or in U.S. Pat. No. 9,767,992, entitled "Microwave Chemical Processing Reactor," which are incorporated herein by reference in their respective entireties for all purposes. The carbon particles, such as the aggregates 132D, can be constructed from several smaller carbon-based constituent elements, such as orthogonally fused FLG and/or SLG, as shown in FIGS. 2B and 2C. Such aggregates can be further deconstructed or disintegrated into their constituent nanoparticles in operation 420 for functionalization of those nanoparticles with nucleophilic functional groups in operation 430 to promote bonding of cross-linkable monomers to exposed carbons. Fragmenting and/or functionalizing can be performed in the reactor in which the aggregates are formed, such as during or immediately after their functionalization. Alternatively, or in addition to in situ (within the same reactor) processing as described, fragmentation and/or functionalization can be done in post-processing operations outside of the reactor, after the aggregates 132D are grown. Nucleophilic moieties added during functionalization can promote coupling with electrophilic moieties of cross-linkable monomers. Nucleophilic moieties can include, for example, hydroxides and/or amines, where in the example of FIG. 4A, exposed carbons can be oxidized to create hydroxylated carbon.

Turning to diagram 400*b* shown in FIG. 4B, nucleophilic moieties of functionalized carbons of operation 430 can be converted to cross-linkable carbons in operation 440 by, for instance, functionalizing one or more exposed surfaces of the structure 130D shown in FIG. 1D with a nucleophilic moiety and adding monomers to exposed and/or active surfaces of carbon nanoparticles. Examples of monomers include portions of oligomers, such as urethanes, polyether, or polyester tethered with acrylates or epoxides. An organic coupler, such as toluene diisocyanate (TDI) or methylene diphenyl diisocyanate (MDI), can also be added in operation 440 to further link bonds between carbon nucleophiles and cross-linkable monomers. The operation 440 can also include combining carbon nanoparticles with a solvent and a polymer initiator, where the polymer initiator will later be used to promote cross-linking of the carbons. Polymer initiators may include ultraviolet (UV) or photoinitiators such as α-hydroxyketones and mono acyl phosphines. Specific examples include Irgacure 184, Irgacure 819, Irgacure 1300, Darocur 1173, and Darocur TPO. Thermal initiators can also (or in the alternative) be used such as benzyol peroxide, 2,2'-azobisisobutyronitrile (AIBN), tert-butyl peroxide, 1,1'-azobis(cyclohexanecarbonitrile), cyclohexanone peroxide, tert-butyl peracetate, and 4,4-azobis(4-cyanovaleric acid). Solvents include, for example, isopropanol, ethanol, 2-methoxyethanol, propylene glycol monomethyl ether acetate, methyl ethyl ketone, cyclohexanone, N-methyl-2-pyrrolidone, N,N-dimethylformamide, xylene, toluene, methylene chloride, and/or various mixtures and combinations thereof.

Materials produced by operation 440 can be used to create an ultraviolet (UV) and/or thermally curable carbon paste by adding solvents and radical initiators. Operation 440 can include washing to remove excess monomers that have not been successfully linked to exposed surfaces of carbon particles such that resulting carbons will have a small number of functional groups on the surfaces of the carbon particles, which can be used for cross-linking. In operation 450, carbon paste is casted as a paste layer 452 and dried onto a substrate 454 (such as any one or more of polyethylene naphthalate, polyethylene terephthalate, polyimide, polycarbonate, and polymethylmethacrylate films) that provides support for the paste layer 452. Solvent in the paste layer 452 can be at least partially removed after being cast onto the substrate 454. In operation 460, pixel patterns for the electrophoretic display are formed by debossing (referring to the techniques of embossing and debossing, which imply the processes of creating either raised or recessed relief images, respectively, and designs in paper and other materials) into a surface of the paste layer, such as by forming a plurality of recesses 463 into a surface of the paste layer 452. After forming the patterns, the cross-linkable carbons in the layer 452 are polymerized into a structure 462 (similar to the structure 130D shown in FIG. 1D) by applying UV energy and/or heat. For example, a metal halide type lamp (such as a UVA light at 320-390 nm, 100 mW/cm$^2$) can be used to cure the surface of the carbon paste layer within 5 minutes of UV exposure. The resulting layer can be further crosslinked by heating the film at 90° C. for 10 minutes. Other free radical polymerization methods known to those having ordinary skill in the art can also or alternatively be used in crosslinking the carbons. The formed structure 462 on the substrate 454 may be incorporated into an EPD, such as the EPD device 100D of FIG. D1.

Carbon-Inclusive Electrophoretic Ink Capsules (Configured to Migrate Through Carbon Structures)

Figure 5:
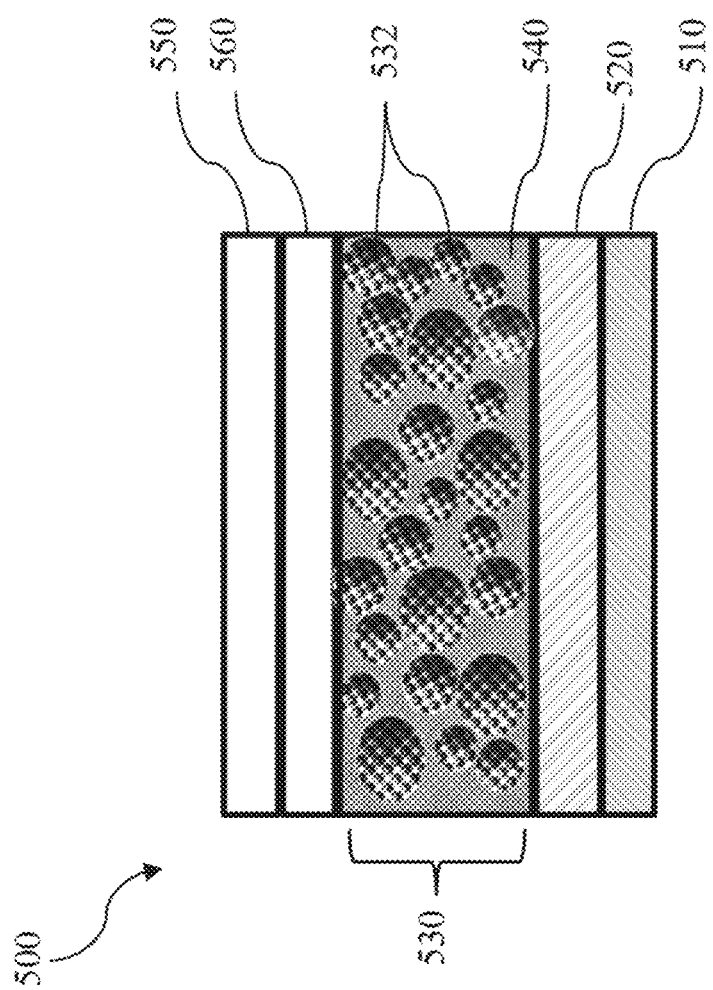
FIG. 5 shows a cross-sectional view of an example electrophoretic visual display, in accordance with some implementations.
Figure 6:
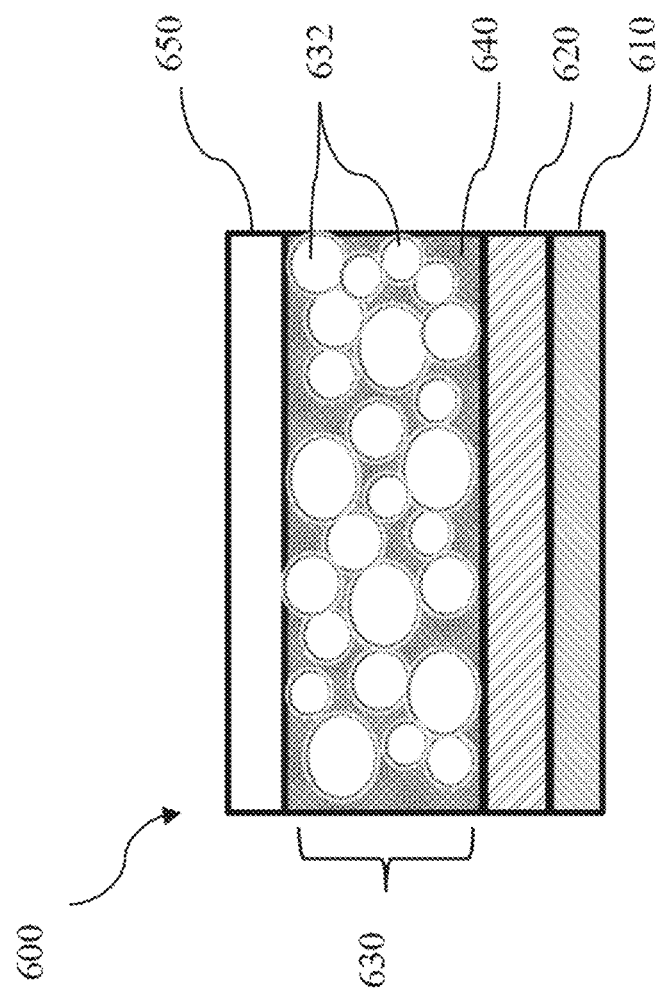
FIG. 6 shows a cross-sectional view of an example electrophoretic visual display, in accordance with some implementations.

FIGS. 5 and 6 show implementations of example EPDs (any one or more of which may be equivalent or similar to EPD 100D shown in FIG. 1D) which use carbon-inclusive electrophoretic inks (interchangeably referred to as electronic inks), in accordance with some implementations. Conventional electrophoretic inks can contain negatively charged white-colored particles and positively charged black-colored particles and be suspended in a clear fluid. The white and black colored particles (referring to charged electrophoretic ink microspheres or capsules) can be organized as a thin film to be incorporated into various end-use applications, such as EPDs, enabling novel applications in phones, watches, magazines, wearables and e-readers, etc., to form detailed human-readable images, where black-colored electrophoretic ink capsules can include carbon black (referring to a material produced by the incomplete combustion of heavy petroleum products such as FCC tar, coal tar, or ethylene cracking tar).

Uniformity in pigment particle size and zeta potential is desirable in EPD device applications, as differences is charged particles can result in corresponding (and undesirable) differences in migration rates upon exposure to an applied electric field, thus resulting in unwanted variation and lack of predictability in resultant image quality. For instance, smaller size particles tend to migrate at a pace faster than larger particles. The presently disclosed electrophoretic inks include any one or more highly structured carbons, such as graphene, carbon nano-onions (CNOs), carbon nanotubes (CNTs), or any combinations or resultant structures derived so as to enable higher particle uniformity than conventional inks as well as a high phase purity of highly structured carbons, rather than carbon black alone. For example, the presented carbon-inclusive electrophoretic inks may have greater than 90% or greater than 95% or greater than 99% of highly structured carbons. The present carbon inks can be fabricated by simultaneously functionalizing and fragmenting carbon particles, resulting in a more uniform distribution of particle sizes and higher dispersion of carbon particles in the ink. For instance, the carbon inks may be monodispersed having a polydispersity index (PDI) of less than 0.1 or have a narrow particle size distribution of <0.2.

The EPD device 500 of FIG. 5 is similar to the EPD device 100D shown in FIG. 1, with a substrate 510 corresponding to the same characteristics as described for substrate 110D, and so on and so forth. Unlike EPD device 100D, device 500 utilizes a carbon-based ink 540 interspersed within a structure 530, and also includes a contrast layer 560 positioned between the structure 530 and second electrode layer 550. Since presence of carbon will cause the carbon ink 540 to be dark in color, the contrast layer 560 can be used to provide a contrasting color so that patterns formed by the carbon ink 540 can be seen by a user when the ink 540 is near the bottom surface of layer 560. For example, contrast layer 560 may be white in color, comprising aluminum dioxide, antimony trioxide, barium sulfate, silicone dioxide, titanium dioxide, zinc sulfide or other white particles, in contrast to a black color of the carbon ink 540.

FIG. 6 shows another EPD display device 600 that can be used with any one or more of the presently disclosed carbon-inclusive inks. The EPD device 600 of FIG. 6 can be substantially similar to the EPD device 100D shown FIG. 1D, with substrate 610 corresponding to the same characteristics as described for substrate 110D, and so on and so forth. Unlike other EPD implementations, EPD device 600 can include a structure 630 of a contrasting color (such as white) to a carbon ink 640, rather than the structure and ink being of the same color as in other example EPD implementations. Structure 630 can be made of polymeric composite materials that include light-colored (such as white) aggregates 632, such as aluminum dioxide, antimony trioxide, barium sulfate, silicone dioxide, titanium dioxide, zinc sulfide or other white-colored aggregates. The aggregates 632 in the structure 630 can be surface functionalized to enable the cross-linking, such as using acrylate functional groups, epoxy groups, or organically modified silica ("OR-MOSIL"). The structure 630 can be light-reflective, making carbon ink unseen when the ink is dispersed away from a viewing surface of the device 600.

Figure 7A:
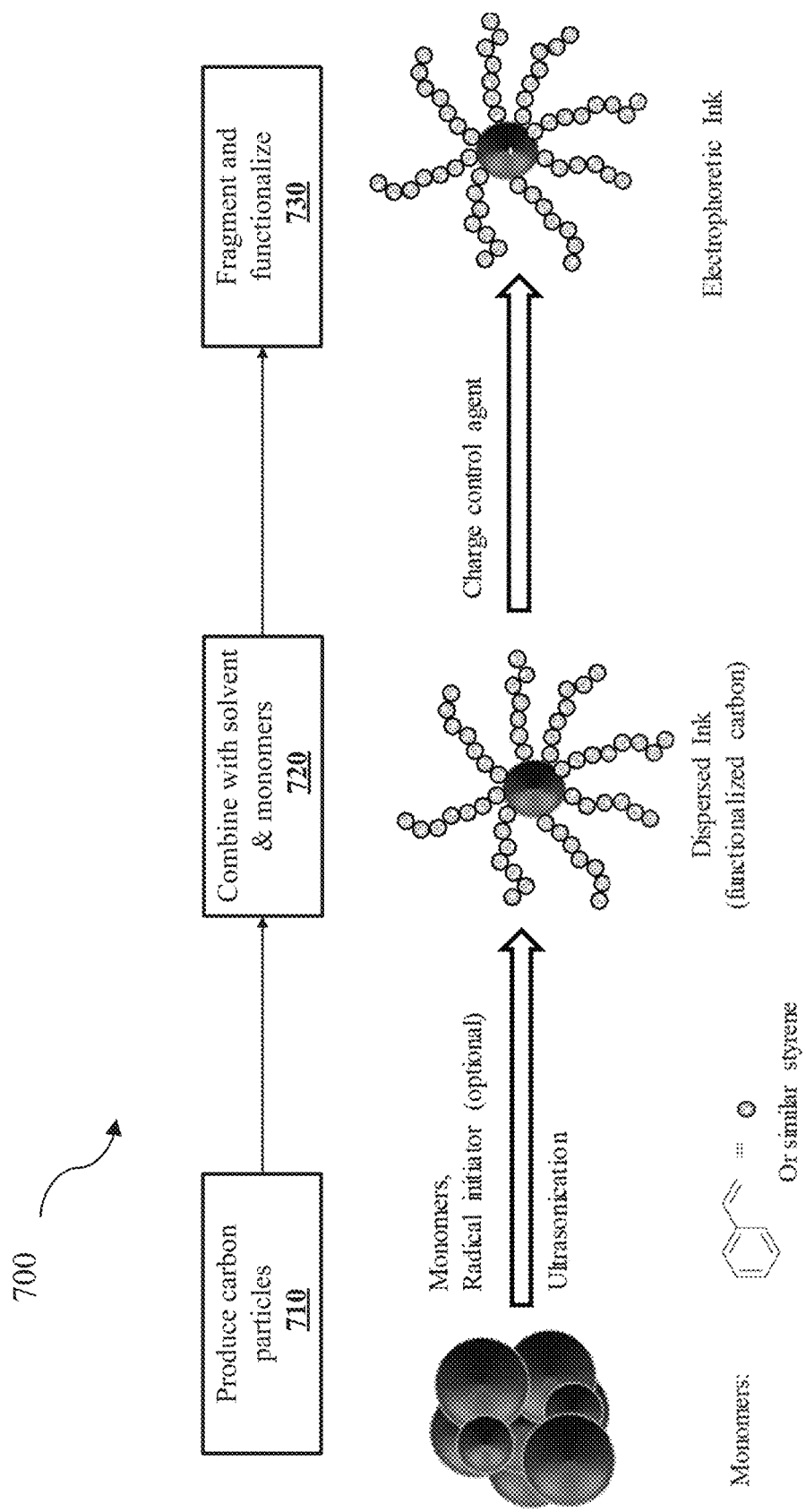
FIG. 7A shows a schematic diagram representing a method of producing a carbon ink for an electrophoretic visual display, in accordance with some implementations.

FIG. 7A illustrates a flowchart 700 with accompanying explanatory schematic diagrams for making carbon inks for EPD devices. In operation 710 of FIG. 7A, carbon particles (similar or equivalent to the aggregates 132D shown in FIG. 1D) are produced using microwave plasma reactors and/or methods as described in any one or more of the aforementioned U.S. Pat. Nos. 9,812,295 and 9,767,992. The carbon particles can be combined with reactive monomers (such as styrene, 4-vinyl-benzyl chloride, and vinyl-benzyl trimethylammonium chloride) in operation 720, where ultrasonic energy is applied to the mixture to simultaneously fragment and functionalize the particles in operation 730. The carbon particles are fragmented into nanoparticles, each of which that may have an average size of, for example, less than 200 nm. The sonication in operation 730 also produces free radicals, allowing the sub-particles to be functionalized with the reactive monomers. The monomers are polymerized on the surfaces of the carbon particles to make linear polymers acting as dispersing agents. The operation 730 may also involve adding a radical initiator, such as AIBN or other thermal initiators. The resulting particles can be dispersed in a low dielectric solvent with a charge control agent (CCA) in operation 730, such as AOT, PIBS, or SPAN, to make a carbon-inclusive electrophoretic ink. Fragmenting and functionalizing can be performed together using ultrasonic energy in operation 730 to create particles that are relatively uniform size and highly dispersed in the electrophoretic ink. Alternatively, carbon nanomaterials can be oxidized that can be coupled with fatty acids (such as oleic acid, isopalmitic acid, and isostearic acid) or amines (such as octadecylamine, hexadecylamine, and oleylamine) to make a functionalized carbon that can be dispersed in a low dielectric solvent. The CCA is then added to increase the zeta potential of the carbon particles. The resulting electrophoretic ink may have a high a zeta potential value of at least 30 mV in magnitude, such as approximately −30 mV to approximately −60 mV (negative values for carbon ink).

Figure 7B:
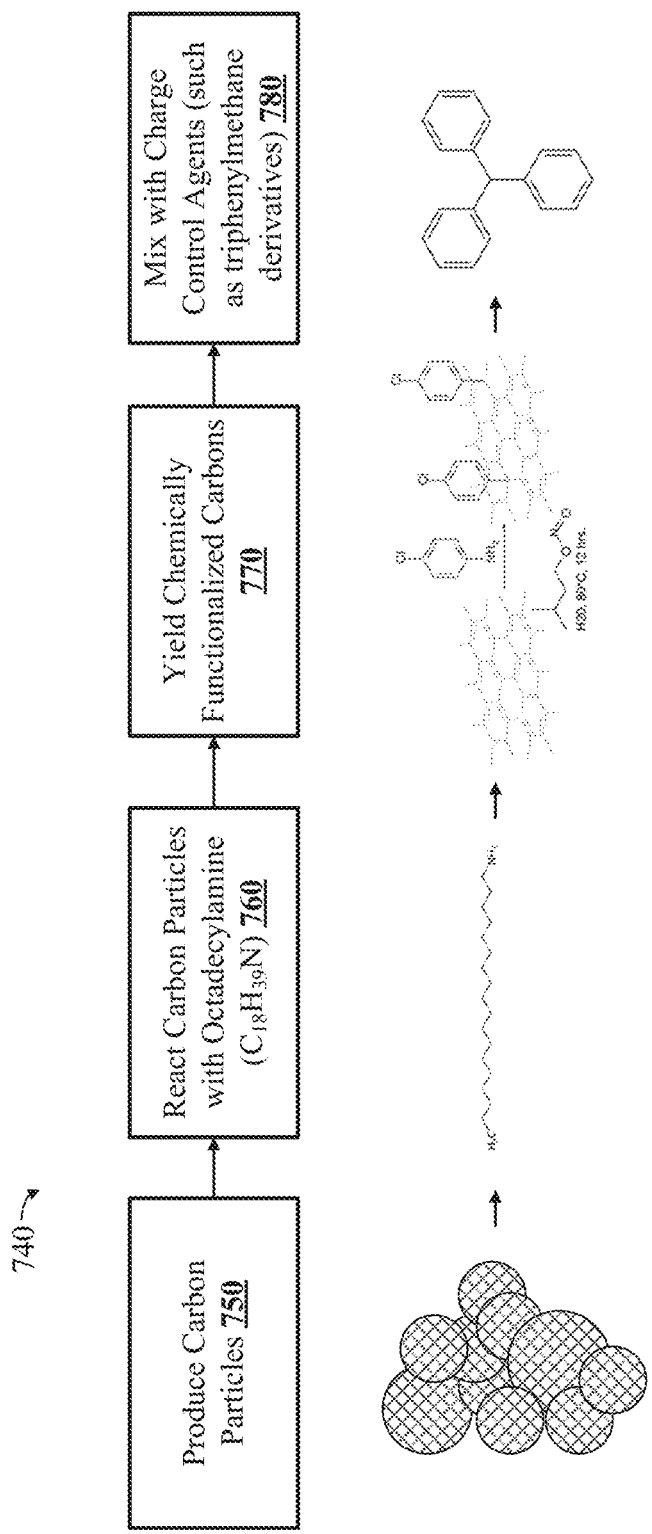
FIG. 7B shows a schematic diagram representing another method of producing a carbon ink for an electrophoretic visual display, in accordance with some implementations.

FIG. 7B is a schematic diagram representing another method 740 of producing a carbon ink for an electrophoretic visual display, in accordance with some implementations. In contrast to that shown and discussed in FIG. 7A, carbon particles can be produced in a manner similar to operation 710 in operation 750 and be reacted with octadecylamine at operation 760 to make functionalized carbon in operation 770. Also, in some configurations of the presently disclosed examples and/or implementations, black or dark-colored carbon-based electrophoretic inks can be used to migrate within a white (or light-colored) stationary carbon-based porous matrix or structure. Such functionalized carbons can then be mixed with charge control agents in operation 780 (such as described in Example 1).

EPD Device Configurations

FIGS. 8-11 illustrate example configurations for any one or more of the EPD devices disclosed herein using the carbon structures (such as the structure 130D shown in FIG. 1D) and/or carbon inks in accordance with some implementations. In these figures, only the electrode layers and matrix layer are shown for clarity. Also, the figures are schematics and are not drawn to scale; for example, dimensions of the recesses and layers may be proportioned differently than what is shown.

Figure 8:
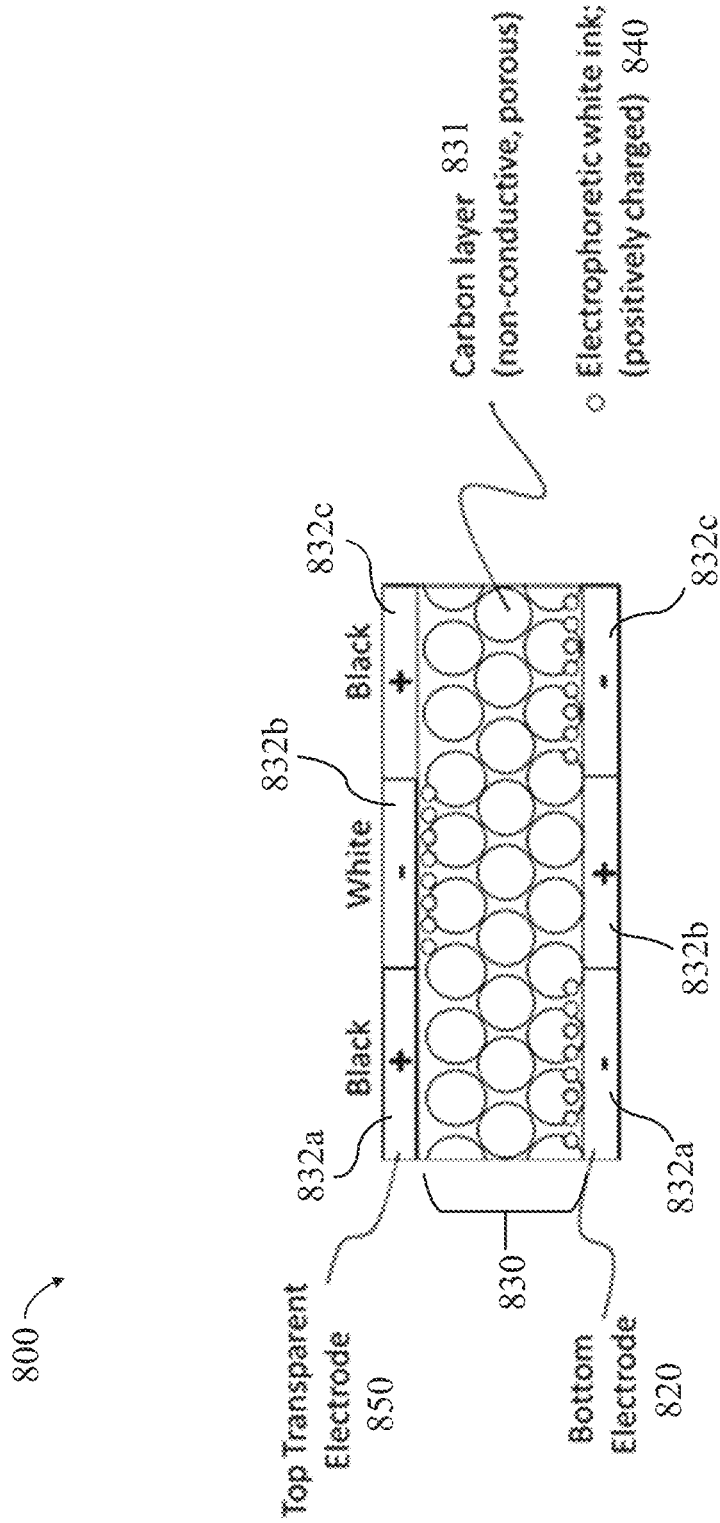
FIG. 8 shows a cross-sectional schematic of an example display configuration for an electrophoretic visual display, in accordance with some implementations.

FIG. 8 shows a portion of an EPD 800 including a first electrode layer 820 ("bottom electrode"), a structure 830 (that can be carbon-based or inclusive similar to structure 130D shown in FIG. 1D) on the first electrode layer 820, and a second electrode layer 850 ("top transparent electrode") on the structure 830. The structure 830 is non-conductive, porous, and made of carbon particles 831. Ink 840 is depicted as droplets in order to illustrate movement of the ink, but it should be understood that ink 840 includes white submicron particles infused into the structure 830 that moves between the pores of the structure 830 as described above. The ink 840 is an electrophoretic white ink and positively charged in this implementation.

The first electrode layer 820 and second electrode layer 850 are shown with pixels 832a, 832b and 832c, where in operation, each pixel of first electrode layer 820 is oppositely charged from the correspondingly paired pixel in the second electrode layer 850. Because ink 840 is positively charged, the ink 840 is attracted to negatively charged pixel 832b of the second electrode layer 850 so that pixel 832b appears white in the EPD 800. Conversely, positively charged pixels 832a and 832c of second electrode layer 850 appear black due to the absence if ink 840 at second electrode layer 850. The pixels 832a, 832b, 832c of the display may have a rectangular, circular, hexagonal, or other shape in the plane of electrode layer 850, where the pixels form a pattern such as an orthogonal or diagonal array.

Figure 9:
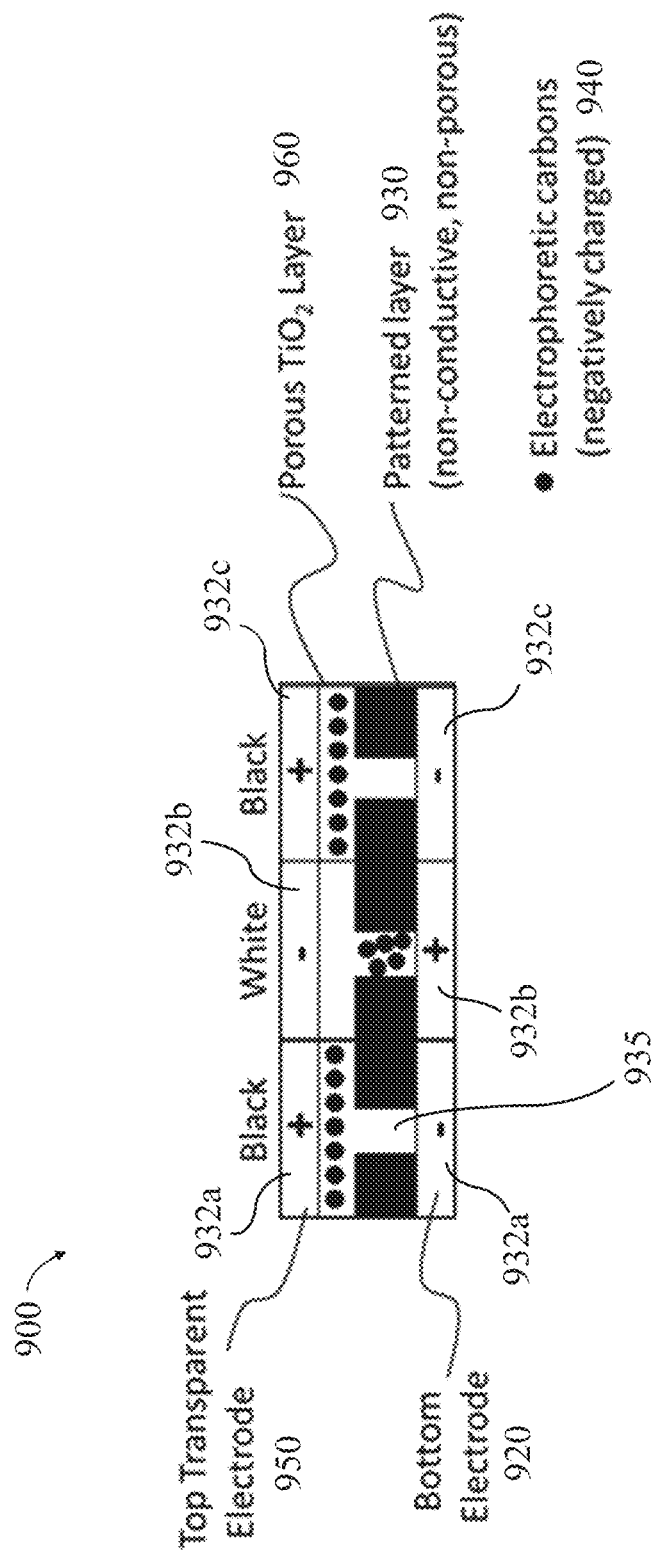
FIG. 9 shows a cross-sectional schematic of an example display configuration for an electrophoretic visual display, in accordance with some implementations.

FIG. 9 is a cross-sectional view of an EPD 900, illustrating an implementation using a non-conductive, non-porous carbon-based structure 930 rather than the structure 830 of FIG. 8. EPD 900 also uses a colored ink 940 instead of a white ink 840. FIG. 9 includes a first electrode layer 920 ("bottom electrode"), the non-porous carbon-based structure 930 on the first electrode layer 920, a porous TiO2 layer 960 on the non-porous carbon-based structure 930, and a second electrode layer 950 ("top transparent electrode") on the layer 960. The non-porous carbon-based structure 930 is patterned, having recessed regions 935 formed in the non-porous carbon-based structure 930 through which the ink 940 can travel. Ink 940 is made of electrophoretic carbons that are negatively charged. The ink 940 may be black or another color, such as by adding a colored pigment instead of the carbon. The pairs of pixels 932a, 932b and 932c in first electrode layer 920 and second electrode layer 950 are similar to the pixels described above for FIG. 8.

In FIG. 9, the pixel 932b is depicted as appearing white with no carbon particles (black ink 940) in the layer 960, and pixels 932a and 932c are depicted as appearing with the color of the ink 940 (ink 940 in porous $TiO_2$ layer 960). Together, the pixels 932a, 932b, 932c form an image on the EPD 900. FIG. 9 shows one implementation of driving the ink, in which the ink 940 moves vertically between the electrode layers 920 and 950 when a voltage is applied between a first electrode in first electrode layer 920 and a second electrode in second electrode layer 950 (such as, electrodes in each pixel 932a,b,c). The electrodes can be individually addressed by addressable arrays in first electrode layer 920 and second electrode layer 950, respectively, as shall be understood by those of ordinary skill in the art. In the example of FIG. 9, the first electrode in pixel 932a of first electrode layer 920 has a negative charge and the second electrode in pixel 932a of second electrode 950 has a positive charge. Because the ink 940 is negatively charged, the ink 940 will move through recess 935, toward second electrode layer 950 and resting within porous layer 960, thus becoming visible in the image produced by the EPD 900. When an opposite voltage is applied, as illustrated by the negative charge on pixel 932b of second electrode layer 950 and a positive charge on pixel 932b of first electrode layer 920, the ink 940 will move back toward electrode layer 920 and the pixel 932b will appear as blank.

Figure 10:
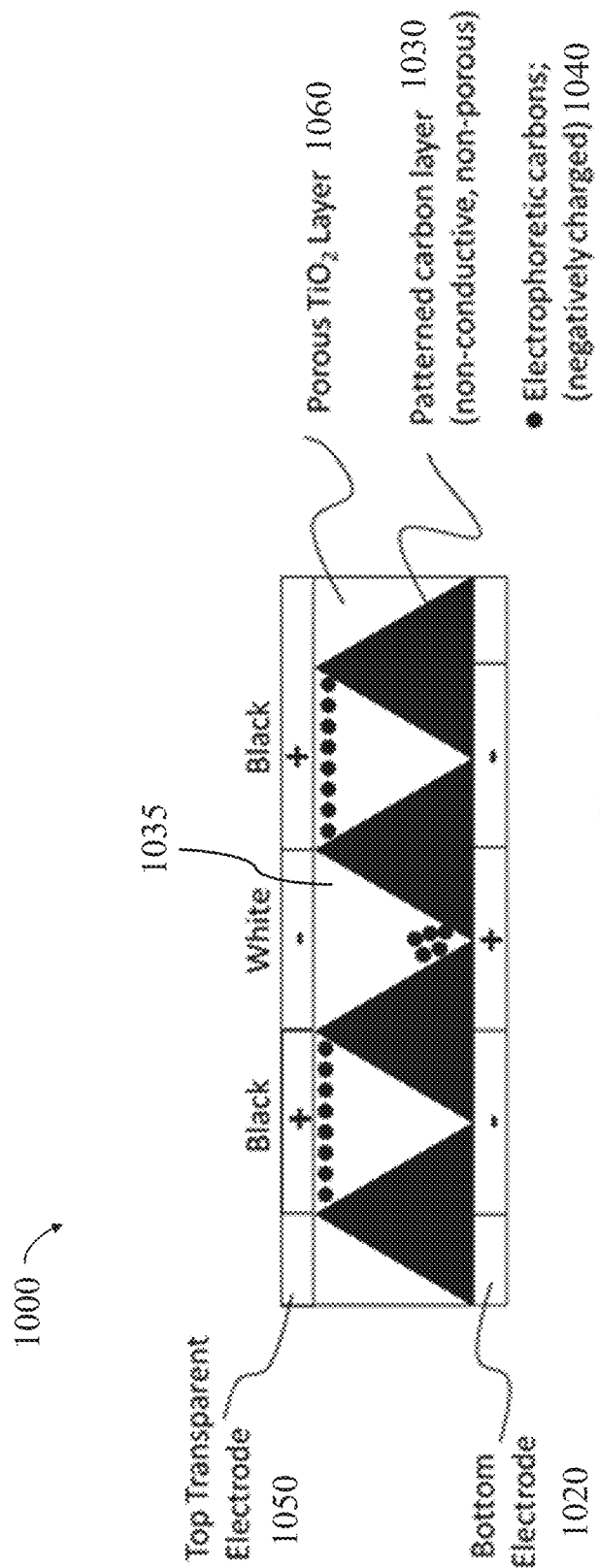
FIG. 10 shows a cross-sectional schematic of an example display configuration for an electrophoretic visual display, in accordance with some implementations.
Figure 11:
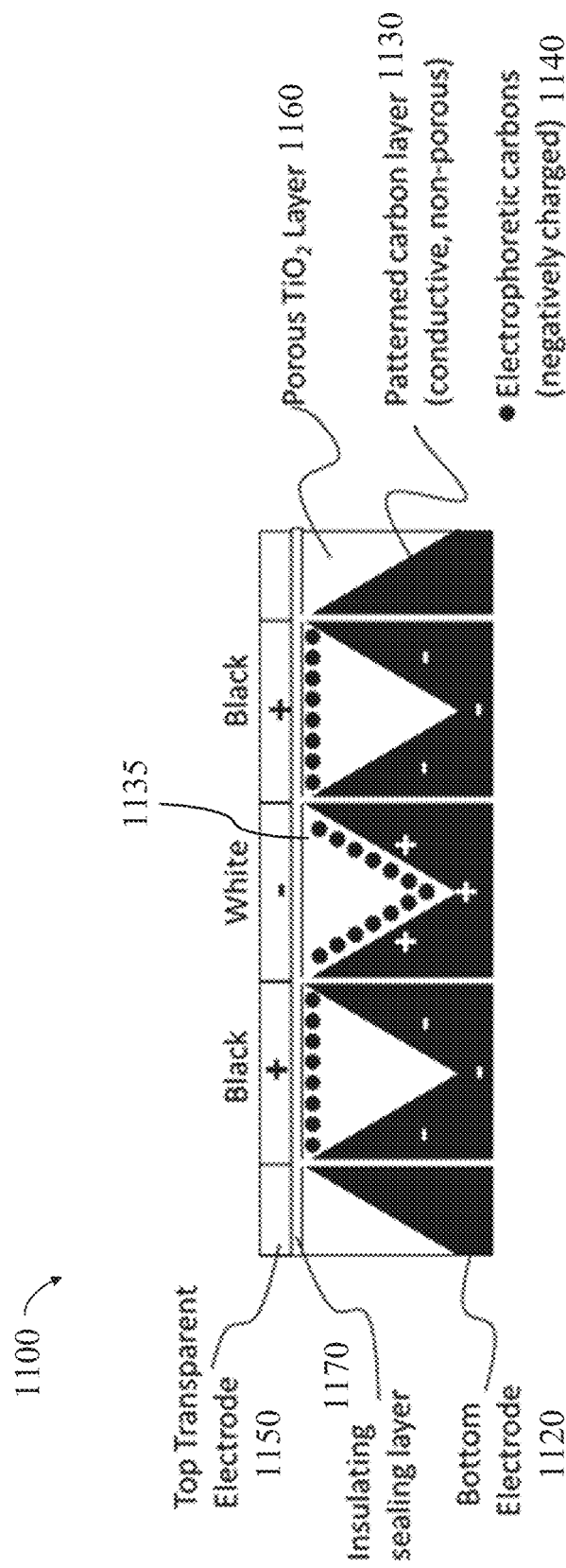
FIG. 11 shows a cross-sectional schematic of an example display configuration for an electrophoretic visual display, in accordance with some implementations.

FIGS. 10 and 11 show implementations of EPDs 1000 and 1100 that are similar to EPD 900 but with openings (such as, recesses) that are triangular in cross-section. EPD 1000 includes a first electrode layer 1020, a non-porous carbon-based structure 1030 on the first electrode layer 1020, a porous TiO2 layer 1060 on the non-porous carbon-based structure 1030, and a second electrode layer 1050 on the porous $TiO_2$ layer 1060. The non-porous carbon-based structure 1030 is non-conductive and non-porous. Recesses 1035 in the non-porous carbon-based structure 1030 have a vertex of the triangular shape that is pointed away from the image viewing surface (such as, away from the second electrode layer 1050). Ink 1040 comprises electrophoretic carbons that are negatively charged. FIG. 10 shows a configuration in which ink 1040 is shuttled vertically in and out of recesses 1035 due to voltage applied to pixels in first electrode layer 1020 and second electrode layer 1050, as described above.

FIG. 11 shows a configuration in which a non-porous structure 1130 is a non-porous layer patterned with triangular recesses 1135 similar to FIG. 10, but the non-porous carbon-based structure 1130 is conductive rather than non-conductive as was the non-porous carbon-based structure 1030. The bottom electrode 1120, top electrode 1150 and porous $TiO_2$ layer 1160 of FIG. 11 are similar to the corresponding layers in FIG. 10. An insulating sealing layer 1170 between porous $TiO_2$ layer 1160 and top electrode 1150 serves to electrically isolate the non-porous structure 1130 from the top electrode 1150. An example of a sealing composition for sealing layer 1170 includes a thermoplastic precursor dispersion that is immiscible with the electrophoretic ink and has lower specific density than the ink. After the immobile phase has been filled with a mixture of sealing precursor and electrophoretic ink, the precursor phase separates and forms a thin layer on the top of the fluid. This layer can then be polymerized thermally or radiologically to hermetically seal the immobile phase. Because the non-porous structure 1130 is conductive, the ink 1140 moves toward the entire faces (such as, side walls) of the triangular recesses 1135 rather than just toward the downward vertex as in FIG. 10. Such an implementation may provide a faster response time in forming an image for the EPD 1100 compared to EPD 1000 since the ink 1140 travels less distance.

Figure 13:
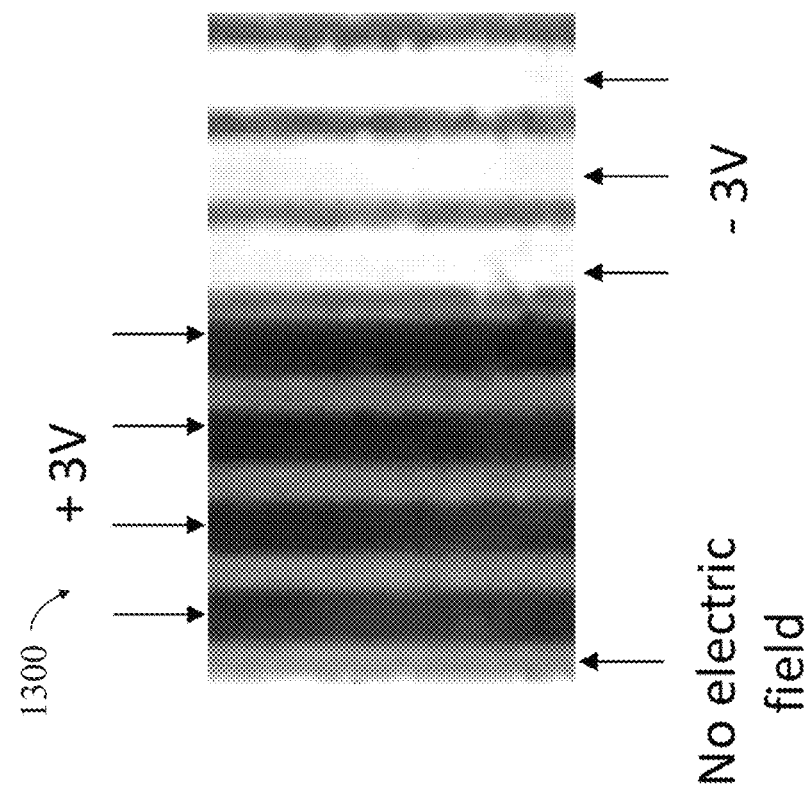
FIG. 13 shows an image of an example electrophoretic display cell, in accordance with some implementations.
Figure 12:
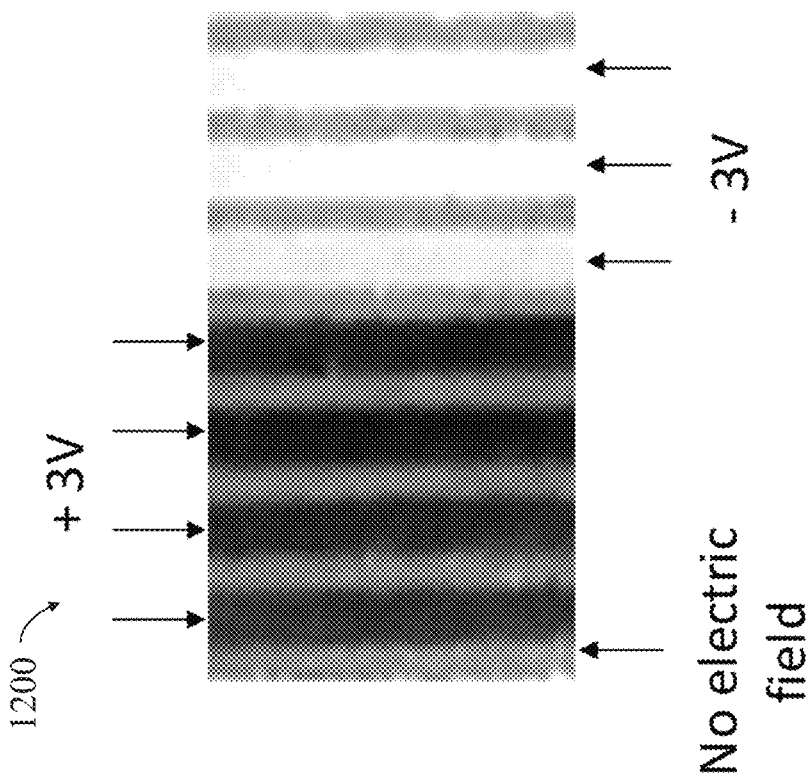
FIG. 12 shows an image of an example electrophoretic display cell, in accordance with some implementations.
Figure 14:
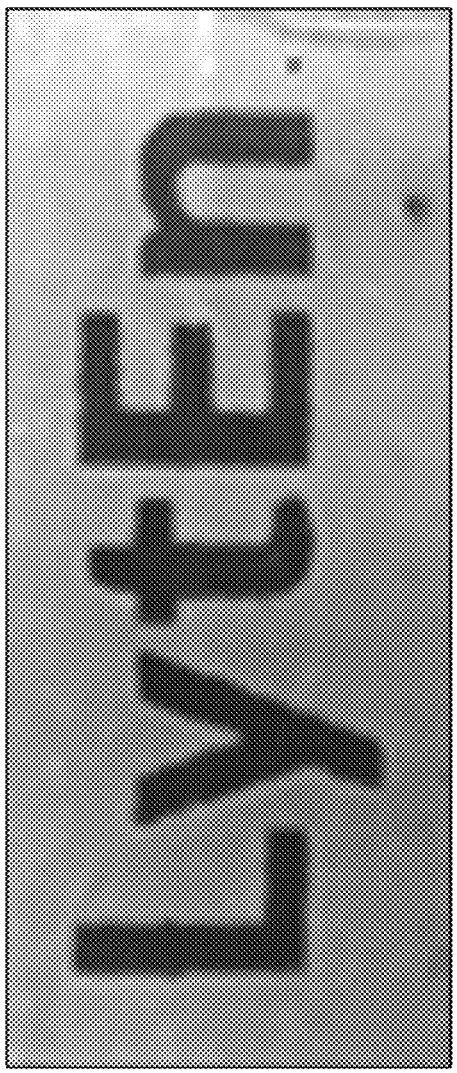
FIG. 14 shows an image of an example electrophoretic display cell, in accordance with some implementations.

FIGS. 12 and 13 show images of an example electrophoretic display cells 1200 and 1300, respectively, in accordance with some implementations. Upon application of a voltage differential of approximately ±1V to any one or more of the display cells 1200 or 1300, a contrasting image was observed (relative to no electric field). Similarly, FIG. 14 shows an image of an example electrophoretic display cell 1400 indicating stylized indicia that can be reconfigured pursuant to voltage applications, suitable for e-readers, supermarket displays, etc., in accordance with some implementations.

Figure 15A:
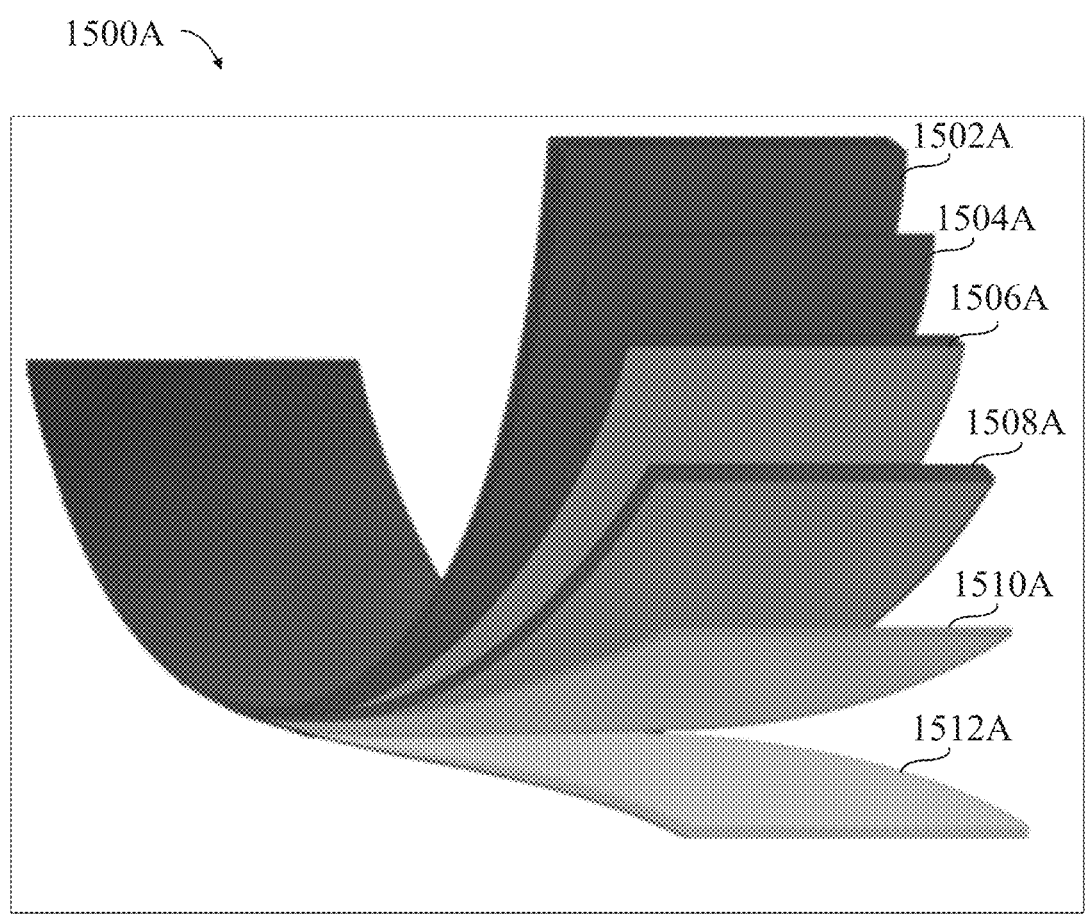
FIG. 15A shows a cut-away schematic diagram of a multi-layered example electrophoretic display, in accordance with some implementations.

FIG. 15A shows a cut-away schematic diagram of an example EPD 1500A (that may be significantly equivalent in structure and functionality to the EPD 130D shown in FIG. 1D and/or any one or more of the presently disclosed EPD devices), in accordance with some implementations. The EPD 1500A can include one or more layers including a protective layer 1502A, a transparent conductive layer 1504A, a porous reflective layer 1506A, a porous carbon matrix with integrated microcells layer 1508A, a sealing layer 1510A, and a flexible layer 1512A (similar to a substrate upon which any one or more of the other layers may be formed or deposited). The protective layer 1502A can be substantially transparent, offering a transparency of greater than 90% in the visible range, and can also be tuned or configured as necessary for particular end-use scenarios, such as for supermarket or grocery applications compared to e-reader applications, etc. The protective layer 1502A can be deposited on top of the transparent conductive layer 1504A, which can have resistance values of approximately (or in the range of approximately) $R_S$<100 Ω/sq→$R_S$<30 Ω/sq. The transparent conductive layer 1504A can be deposited on the porous reflective layer 1506A, which is optional in some configurations and can be implemented based on the color of carbon-based ink. The porous reflective layer 1506A can be deposited on the porous carbon matrix with integrated microcells layer 1508A, which may be substantially equivalent in form and functionality to the structure 130D shown in FIG. 1D, an include porosity sized at approximately 20 μm, or at other sizes pursuant to, for instance, the size of carbon-inclusive electrophoretic ink particles or capsules used, etc. The porous carbon matrix with integrated microcells layer 1508A can be deposited on the sealing layer 1510A, which can be configured to include or otherwise be adjoined or held together by a carbon-doped polymer. The sealing layer 1510A can be deposited on a flexible layer 1512A which can substantially mimic the functionality of any one or more of the presently disclosed substrates to complete the multi-layered example EPD 1500A.

FIG. 15B shows a listing of features 1500B associated with a multi-layered electrophoretic display, in accordance with some implementations. A top electrode (not shown in FIG. 15A) to be used with the example EPD 1500A can include or be formed by optically transparent conductors that are conductive, but do not contain silver (Ag). The porous carbon matrix with integrated microcell layer 1508A can include patterned Microcups, microcapsules, or recessed regions that are configured to enhance electrophoretic ink migration therein, resulting in optimal image formation quality at reduced power consumption levels. A first and second electrode layer (not shown in FIG. 15A) can be prepared to be solvent-resistant. All transparent components of the example EPD 1500A can be carbon-inclusive, such as including any one or more of the highly structured carbons associated with the presently disclosed implementations.

Figure 16A:
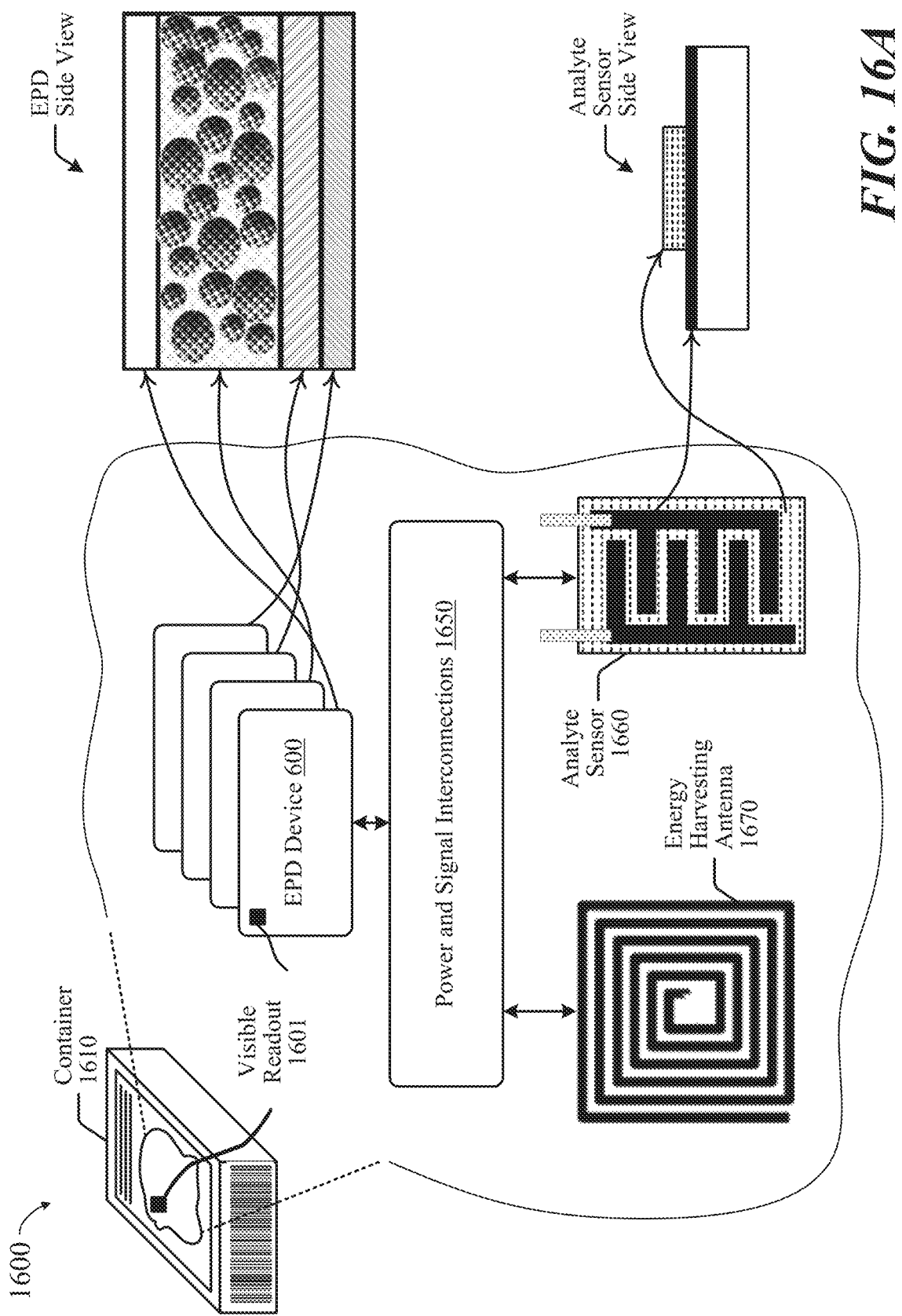
FIG. 16A shows an example implementation of a multi-layered electrophoretic display, in accordance with some implementations.

FIG. 16A shows an example implementation of a multi-layered electrophoretic display 1600 that is disposed on a container 1610. The multi-layered electrophoretic display 1600 may be the same as or a variation of the EPD device 600 as heretofore described. In this example, the EPD device 600 is disposed in proximity to other components that interoperate to form a sensor system with a visible readout 1601. In some cases, and as shown, the container (e.g., shipping carton, envelope, etc.) has surfaces upon which one or more sensors and a visible readout device can be printed. In some cases, the one or more sensors and one or more visible readout devices are interconnected so as to form an analyte sensor system that can be printed (e.g., 3D-printed, inkjet-printed, photolithographically-printed, etc.) onto one or more labels, which are turn affixed to containers.

FIG. 16A shows an exploded view of a sample configuration of a set of components that interoperate to form an analyte sensor system for detecting fluid (e.g., gaseous or liquid) analytes, and for displaying (e.g., a visible readout 1601) an indication of presence, and/or concentration of the analyte. The multi-layered electrophoretic display may be composed of any number and/or juxtaposition of pixels. The analyte sensors of the analyte sensor system may be electrochemical, high frequency, resonant, chemiluminescent, or any combination of these. In some cases, first analyte sensor and second analyte sensor are printed on the same substrate (e.g., label or surface of a container). Each analyte sensor can include a first electrode, a second electrode and an electrolyte, some of which components include particulate carbon and redox mediators. An array of analyte sensors can be used to add functionality, such as the ability to detect multiple gases, and/or to subtract a background level of moisture and/or to improve the sensitivity to any particular analyte. As shown, an EPD device 600 is coupled to an analyte sensor 1660 through power and signal interconnections 1650.

Multiple analyte sensors disposed on one container can be cooperatively utilized so as to detect a combination of chemicals, which in turn leads to a characterization an overall compound. The presence of multiple analyte sensors can be used to rule out false positives. Such multiple analyte sensor systems can include a first sensor configured to detect a first target chemical, and a second sensor configured to detect a second target chemical that is different from the first target chemical. An indicator such as the shown EPD device 600 renders a visual indication if and when both the first sensor positively detects the first target chemical and the second sensor positively detects the second target chemical. For example, a first concentric ring might be displayed (e.g., as a visible readout 1601) if and when the first sensor positively detects the first target chemical and a second concentric ring might be displayed if and when the second sensor positively detects the second target chemical.

Still further, other components can be integrated with the analyte sensor system to add additional functionality to the analyte sensor system. For example, an energy harvesting antenna 1670 can provide the electrical power needed for the sensor and/or for the display. Further details regarding general approaches to making and using an energy harvesting antenna are described in U.S. application Ser. No. 16/282,895 titled "Antenna with Frequency-Selective Elements", filed on Feb. 22, 2019, which is hereby incorporated by reference in its entirety.

As another example for providing electrical power needed for the sensor and/or for the display, an energy storage device (not shown) can be disposed in proximity to the sensor and/or for the display. Further details regarding general approaches to making and using an energy storage device are described in U.S. application Ser. No. 16/740,381 titled "MULTI-PART NONTOXIC PRINTED BATTERIES", filed on Jan. 10, 2020, which is hereby incorporated by reference in its entirety.

Strictly as non-limiting variations of electro-active labels having a display system printed thereon, the electro-active labels can contain EPD devices that are configured to display telemetry, Q-codes or bar codes, and/or icons. Example variations include telemetry where information can be updated, and/or have an image (e.g., a gauge image, a Q-code image, a QR code image, or bar code image, etc.) using digital data and/or any variations of alpha or alphanumeric text formats. In some implementations, a color change or image change is displayed in a sequence. In such implementations, a change in the display, such as a change in a displayed symbol or color or colors of an image, or a time-sequenced back-and-forth change, can be used to indicate any then-current condition such as the condition of the surrounding environment, or change in the display serve to indicate the presence of an analyte, or condition of the contents of the container, etc.

The foregoing devices can also optionally include low power communications components, such as may be configured to communicate with other electronic devices. In some non-limiting examples, a cardboard shipping container is equipped with a first electrochemical sensor similar to analyte sensor 1660, and a second electrochemical sensor that is a variant of analyte sensor 1660. The energy harvesting and/or energy storage devices drive the sensors and display devices.

The beneficial properties of the particulate carbon coupled with the foregoing sensor designs enables very low power devices, such as devices that operate on currents from 0.1 microamps to 5 microamps, and at voltages around 1 volt. This example illustrates that analyte sensors utilizing the particulate carbon described herein can be produced using low cost low power driver/detection electronics that can be integrated onto the surfaces of even small packages. Furthermore, this example shows that such low cost printed displays can also be integrated with other system components such as analyte sensors, energy harvesters, batteries, and communication chips.

In some cases, and as shown in FIG. 16B, two different sets of components may be printed on two different substrates, and then, at point of use, the two different substrates can be combined into a single detection and display system. In this and other detection and display systems, the characteristics of a first set of components 1661 might be different from the characteristics of a second set of components 1662, and as such, the first set of components 1661 might be disposed on a first substrate 1641 and the second set of components 1662 might be disposed on a second substrate 1642. Electrical connectivity (e.g., for power and/or for electrical signaling), can be provided through mated electrically conductive terminals. In the example of FIG. 16B, mated positive polarity terminals (e.g., first plus terminal 1651, second plus terminal 1652) and mated negative polarity terminals (e.g., first minus terminal 1653, second minus terminal 1654) provide power. In other implementations, additional mated pairs of terminals can be configured to provide signaling between members of the first set of components 1661 and members of the second set of components 1662. Moreover, in situations when the characteristics of a first set of components 1661 are different from the characteristics of the second set of components 1662, the printing techniques might differ as pertaining to forming the first set of components 1661 on the first substrate 1641 and as pertaining to forming the second set of components 1662 on the second substrate 1642.

Any of the aforementioned printing techniques can be employed to construct various ones of the devices of the first set of components or the second set of components 1662. In some cases, the constituents and/or characteristics of any one or more layers of the components might indicate use of high-energy photolithography. More specifically, in cases where a slurry is needed (e.g., to form an electrolyte), and/or when a 3D structure is deeper in a depth dimension than can be formed using the foregoing 3D printing techniques, and/or when a binder is needed to provide mechanical integrity to a portion of a device, and/or when higher throughput than can be provided using additive 3D printing techniques is needed, then use of subtractive high-energy photolithography might be indicated. In some cases, the first set of components of the first substrate is printed using a first printing technique, whereas the second set of components of the second substrate is printed using a second printing technique.

Strictly as one example and referring again to the second set of components 1662 that is disposed on second substrate 1642, the second set of components might be formed through use of photolithography using light having a wavelength in the ultraviolet range. More specifically, various techniques for performing vacuum ultraviolet (VUV) lithography can be applied.

In some cases, the pressures involved when performing VUV lithography might be at pressures other than vacuum or near-vacuum. In fact, some printing/depositing techniques are at pressures much higher than atmospheric. Furthermore, to support a wide range of pressures used when performing VUV lithography, the irradiating wavelength is selected to be in a region of low air absorption such that a vacuum environment is not necessary in order to perform high-energy photolithography. This flexibility with respect to wavelengths and pressures in use when performing VUV lithography leads to higher printing throughput.

The selection of light wavelengths (in the range of about 120 nm to about 172 nm, which correspond to photon energies of about 7 eV to about 10.1960 eV), results in desired feature sizes being achieved. In the context of the present disclosure, small feature sizes (e.g., 1 micron, 0.5-micron, 0.25 micron, and smaller) can lead to smaller and smaller display pixels, which in turn leads to displays having higher and higher resolutions.

EXAMPLES

Example 1, Electrophoretic Ink 1

Graphene was prepared using any one or more of the aforementioned techniques and/or a method reported in U.S. Pat. No. 9,812,295, entitled "Microwave Chemical Processing," or in U.S. Pat. No. 9,767,992, entitled "Microwave Chemical Processing Reactor." 10 g of graphene was added to 250 mL of 96% sulfuric acid cooled in an ice bath, and the resulting mixture was stirred for at least 90 minutes. 50 g of $KMnO_4$ was slowly added to the reaction mixture to prevent any heating. After stirring for 30 minutes, the reaction mixture was heated to 35 C and stirred for additional 2 hours. 450 mL of H2O and 50 mL of $H_2O_2$ were added initially, and then additional 700 mL of $H_2O$ was added. The reaction mixture was filtered and wash with 5% HCl and plenty of $H_2O$ until the eluent pH reached 7 to yield graphene oxide.

300 mg of the graphene oxide was dispersed and sonofragmented in 30 mL of $H_2O$ using a probe sonicator set at 30% amplitude (Sonics VCX 750) for 2 hours. Sonication resulted in submicron particles with an average particle size diameter of 149 nm, which was measured using a dynamic light scattering method. Next, 500 mg of octadecylamine (ODA) in 50 mL of ethanol was added and refluxed overnight. Resulting ODA functionalized graphene particles were washed with 50 mL of $H_2O$, followed by 3×50 mL of ethanol. To make an electrophoretic ink, 150 mg of the ODA functionalized graphene was mixed with 150 mg of Span 80 in 3.75 g of 1,2,3,4-tetrahydronaphthalene (tetraline). The mixture was mixed in a sonication bath for 1 hour and then filtered through 0.7 um glass fiber filter to yield the electrophoretic graphene ink.

Example 2, Electrophoretic Ink 2

Example 1 was repeated with carbon nano-onions (CNO) instead of graphene to make a CNO based ink.

Example 3, Electrophoretic Ink 3

900 mg of graphene was dispersed in 90 mL of $CH_2Cl_2$ and irradiated with a sonication probe at 20 kHz at 0° C. After 2 hours of sonication, the average particle size was 191 nm, which was measured using a dynamic light scattering method. To the fragmented carbon dispersion, 9.0 g of tetrabutylammonium bromide in 15 mL of H2O, 1.2 g of $KMnO_4$ in 15 mL of H2O, and 40 mL of acetic acid were added, and the mixture stirred overnight. Resulting graphene hydroxide was washed with aqueous ethanol (50 wt %, 100 mL) for at least 5 times to remove impurities. 5 g of oleic acid was added to 500 mg of graphene hydroxide in 100 mL of hexane, and the mixture was stirred at 60° C. for 20 hrs. Oleic acid functionalized carbon was obtained by centrifugation, which was washed with 30 mL of hexane at least three times. To make an electrophoretic ink, 100 mg of the oleic acid functionalized graphene was mixed with 100 mg of Span 85 in 2.5 g of dodecane. The mixture was mixed in a sonication bath for 1 hour and then filtered through 0.7 μm glass fiber filter to yield the electrophoretic ink.

Example 4, Electrophoretic Ink 4

2 g of graphene, 100 mg of benzoyl peroxide, 350 g of styrene, and 700 mL of toluene were added to a round bottle flask. The reaction mixture was degassed by bubbling argon for 1 hour before irradiating with high intensity ultrasound at 20 kHz for 2 hours at 0° C. The mixture was filtered through a Teflon filter (0.22 um) and washed with toluene at least three times. The polystyrene functionalized graphene (100 mg) was dried and redispersed in xylene (2.5 g) with 100 mg of Span 85 using a sonication bath to make the electrophoretic ink Example 5, Cross-Linkable Carbon Materials 10 g of graphene hydroxide prepared in Example 3 was dispersed in 1 L of DMF with an ultrasonicator. After the dispersion solution was degassed with nitrogen, 0.5 mL of dibutyltin dilaurate was added, and 300 g of toluene diisocyanate pre-dissolved in 200 mL of DMF was added dropwise at 70° C. After 4 hours of stirring, the reaction mixture was cooled to 50° C., and then 300 g of hydroxyethyl acrylate was added dropwise, and the mixture was stirred for additional 12 hours. Finally, the acrylate functionalized graphene was obtained by vacuum filtration and washing with methylene chloride. To make a cross-linkable carbon formulation, 10 g of the acrylate functionalized graphene was dispersed in 10 mL of a 1:1 mixture of ethanol and xylene, along with 500 mg of Darocur 1173 and 500 mg of benzoyl peroxide. The resulting formulation was mixed with a mechanical stirrer Example 6, Electrophoretic Display Cell 1

An ITO coated PET was coated with the cross-linkable carbon formulation prepared as described in Example 5 using a doctor blade with a 50 μm gap. After the solvent was removed, the resulting film was cured with a UVA light at 100 mW/cm2 for 5 mins, which was following by 90° C. heat treatment for 10 mins. A separate ITO coated glass was coated with titanium dioxide/polyacrylate composite materials. Electrophoretic Ink 1 was added between the ITO glasses and then sealed using an epoxy sealant. Applying ±1V to the display cell showed a contrasting image as shown FIG. 12

Example 7, Electrophoretic Display Cell 2

Example 6 was repeated using Electrophoretic Ink 2 as demonstrated in FIG. 13

Example 8, Electrophoretic Display Cell 3

Example 6 was repeated using Electrophoretic Ink 2 as demonstrated in FIG. 14, to form a text image.

Reference has been made to implementations of the disclosed invention. Each example has been provided by way of explanation of the present technology, not as a limitation of the present technology. In fact, while the specification has been described in detail with respect to specific implementations of the invention, it will be appreciated that those skilled in the art, upon attaining an understanding of the foregoing, may readily conceive of alterations to, variations of, and equivalents to these implementations. For instance, features illustrated or described as part of one implementation may be used with another implementation to yield a still further implementation. Thus, it is intended that the present subject matter covers all such modifications and variations within the scope of the appended claims and their equivalents. These and other modifications and variations to the present invention may be practiced by those of ordinary skill in the art, without departing from the scope of the present invention, which is more particularly set forth in the appended claims. Furthermore, those of ordinary skill in the art will appreciate that the foregoing description is by way of example only and is not intended to limit the invention.

What is claimed is:

1. An electrophoretic display system, comprising:
a first electrode disposed on a substrate;
a second electrode disposed on the substrate; and
a three-dimensional (3D) carbon-based structure disposed between the first and second electrodes, the 3D carbon-based structure configured to guide a migration of electrically charged electrophoretic ink particles dispersed throughout the 3D carbon-based structure, the electrically charged electrophoretic ink particles responsive to application of a voltage on the first electrode, the 3D carbon-based structure comprising:
- a plurality of 3D aggregates comprising graphene nanoplatelets orthogonally fused together and cross-linked by a polymer; and
- a plurality of channels interspersed throughout the 3D carbon-based structure and comprising at least one of an inter-particle pathway or an intra-particle pathway.

2. The electrophoretic display system of claim 1, wherein the intra-particle pathways are of a smaller dimension than the inter-particle pathways.

3. The electrophoretic display system of claim 1, further comprising a plurality of recesses formed in any one or more of the plurality of 3D aggregates or the plurality of channels.

4. The electrophoretic display system of claim 1, wherein the inter-particle pathways have an average radial dimension no greater than approximately 10 μm.

5. The electrophoretic display system of claim 1, wherein the intra-particle pathways have an average radial dimension greater than approximately 200 nm.

6. The electrophoretic display system of claim 1, wherein each 3D aggregate further comprises any one or more of graphene, carbon nano-onions, carbon nanoplatelets, or carbon nanotubes.

7. The electrophoretic display system of claim 1, wherein the polymer includes any one or more of cellulose, cellulose acetate butyrate, styrene butadiene, polyurethane, polyetherurethane, acrylate, epoxy, or vinyl.

8. The electrophoretic display system of claim 1, wherein the 3D carbon-based structure is independent of any one or more of microcups or microcapsules.

9. The electrophoretic display system of claim 1, wherein the electrically charged electrophoretic ink particles further comprises a plurality of negatively charged mobile titania particles.

10. The electrophoretic display system of claim 9, wherein the negatively charged mobile titania particles are configured to display a substantially white coloration.

11. The electrophoretic display system of claim 1, wherein the 3D carbon-based structure is in a non-electrically conductive state.

12. The electrophoretic display system of claim 1, further comprising an antenna configured to provide power to the display system.

13. The electrophoretic display system of claim 1, further comprising a contrast layer disposed between the 3D carbon-based structure and the pair of electrodes.

14. The electrophoretic display system of claim 13, wherein the contrast layer is a first color, and the plurality of electrically charged electrophoretic ink particles is a second color that is different from the first color.

15. The electrophoretic display system of claim 13, wherein the contrast layer is white in color.

16. The electrophoretic display system of claim 15, wherein the contrast layer comprises any one or more of aluminum dioxide, antimony trioxide, barium sulfate, silicon dioxide, titanium dioxide, or zinc sulfide.

17. The electrophoretic display system of claim 15, wherein the electrophoretic ink is carbon based.

18. The electrophoretic display system of claim 17, wherein the ink comprises one or more of graphene, carbon nano-onions (CNOs), or carbon nanotubes (CNTs).

19. The electrophoretic display system of claim 1, wherein the 3D carbon-based structure is defined by a polydispersity index of less than approximately 0.5.

* * * * *